(12) United States Patent
Heijkants et al.

(10) Patent No.: US 7,943,678 B2
(45) Date of Patent: May 17, 2011

(54) METHOD FOR THE PREPARATION OF NEW SEGMENTED POLYURETHANES WITH HIGH TEAR AND TENSILE STRENGTHS AND METHOD FOR MAKING POROUS SCAFFOLDS

(75) Inventors: Ralf Guillaume Jean Catharina Heijkants, Groningen (NL); Albert Johan Pennings, Maaseik (BE); Jacqueline Hermina De Groot, Groningen (NL); Ralph Vincent Van Calck, Preston (GB)

(73) Assignee: Orteq, B.V., Groningen (NL)

( * ) Notice: Subject to any disclaimer, the term of this patent is extended or adjusted under 35 U.S.C. 154(b) by 624 days.

(21) Appl. No.: 10/546,512

(22) PCT Filed: Feb. 19, 2004

(86) PCT No.: PCT/NL2004/000128
§ 371 (c)(1),
(2), (4) Date: Jun. 28, 2006

(87) PCT Pub. No.: WO2004/074342
PCT Pub. Date: Sep. 2, 2004

(65) Prior Publication Data
US 2007/0015894 A1    Jan. 18, 2007

(30) Foreign Application Priority Data
Feb. 19, 2003    (EP) .................................... 03075487

(51) Int. Cl.
*C08J 9/26* (2006.01)
*C08J 9/28* (2006.01)
*C08G 18/08* (2006.01)
*C08G 18/10* (2006.01)
*C08G 18/42* (2006.01)

(52) U.S. Cl. ................ 521/64; 264/41; 264/49; 521/61; 521/63; 521/155; 521/159; 521/170; 521/172; 521/173

(58) Field of Classification Search .................. 521/61, 521/63, 64, 155, 159, 170, 172, 173; 264/41, 264/49
See application file for complete search history.

(56) References Cited

U.S. PATENT DOCUMENTS

| | | | |
|---|---|---|---|
| 3,428,610 A | | 2/1969 | Wolfgang |
| 5,374,704 A | * | 12/1994 | Muller et al. .................. 528/66 |
| 5,969,020 A | * | 10/1999 | Shalaby et al. ................ 524/167 |
| 6,302,916 B1 | * | 10/2001 | Townley et al. ........... 623/23.58 |
| 6,472,210 B1 | * | 10/2002 | Holy et al. .................... 435/395 |
| 2001/0034429 A1 | | 10/2001 | Bruchmann et al. |
| 2002/0005600 A1 | | 1/2002 | Ma |

FOREIGN PATENT DOCUMENTS

| | | |
|---|---|---|
| EP | 0 548 745 A | 6/1993 |
| WO | 99/25391 A | 5/1999 |
| WO | 99/64491 A | 12/1999 |

OTHER PUBLICATIONS

Oertel; Polyurethane Handbook Chemistry—Raw Materials—Processing—Application—Properties, Second Edition; Hanser Publishers; New York; 1993; pp. 26 and 27.*

* cited by examiner

*Primary Examiner* — Rabon Sergent
(74) *Attorney, Agent, or Firm* — Kenyon & Kenyon LLP

(57) ABSTRACT

The invention presents a new method to prepare biomedical polyurethanes with high tensile and tear strengths. Such polyurethanes are especially interesting for making foams thereof, e.g. as meniscus implants. A new method, applicable to the biomedical polyurethanes, has been found to make such foams, that can be used as scaffolds. This method is based on salt leaching and phase separation.

25 Claims, 7 Drawing Sheets

Figure 1:
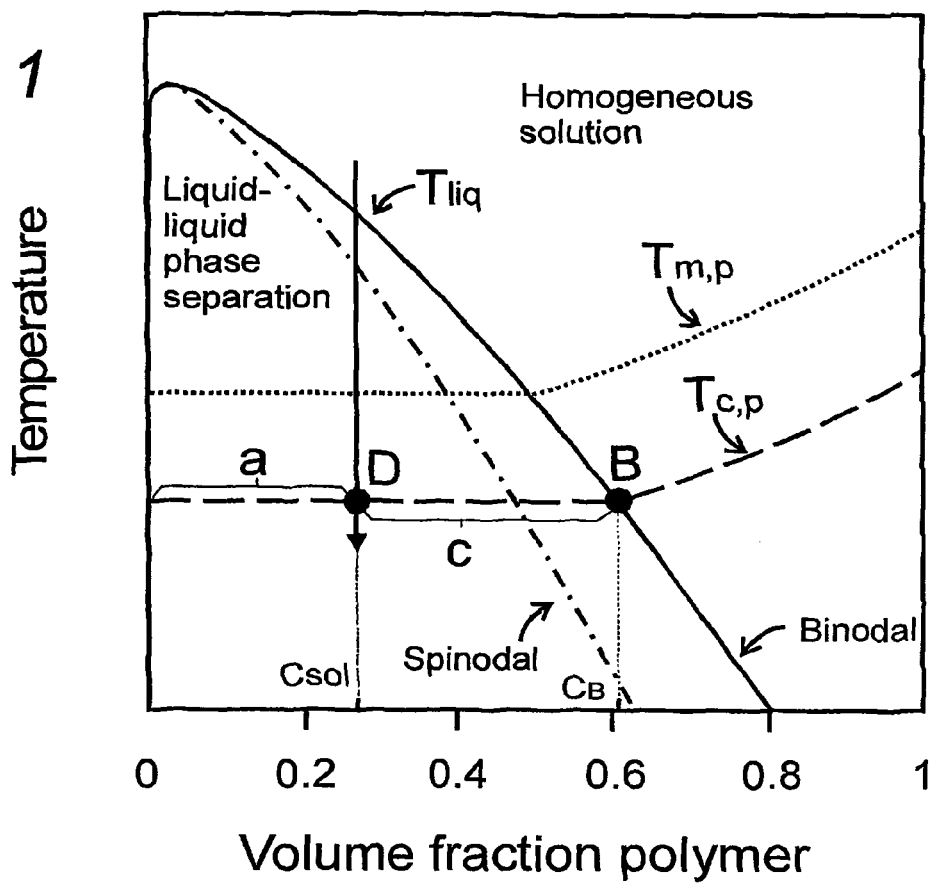

Fig 7
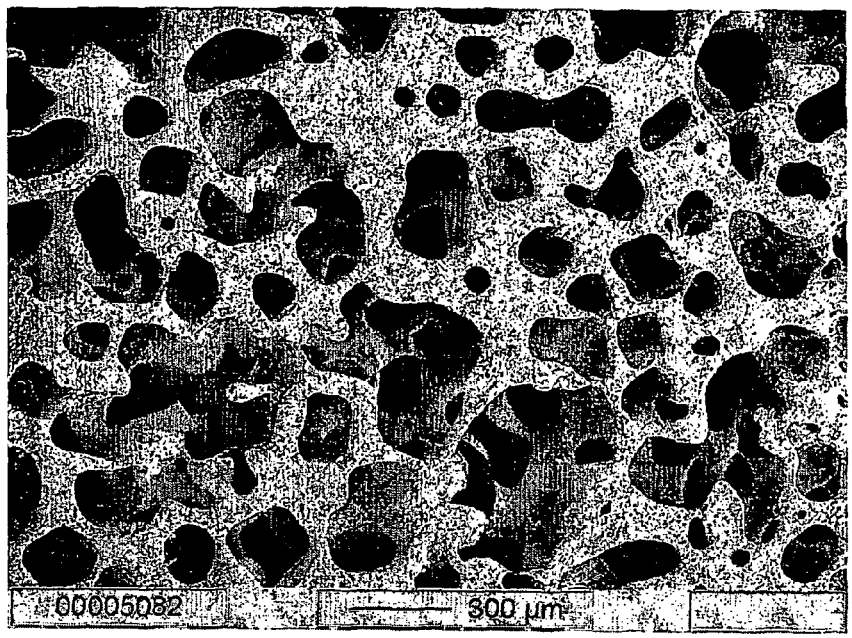
Fig 8  PCL 2000 with stannous octoate
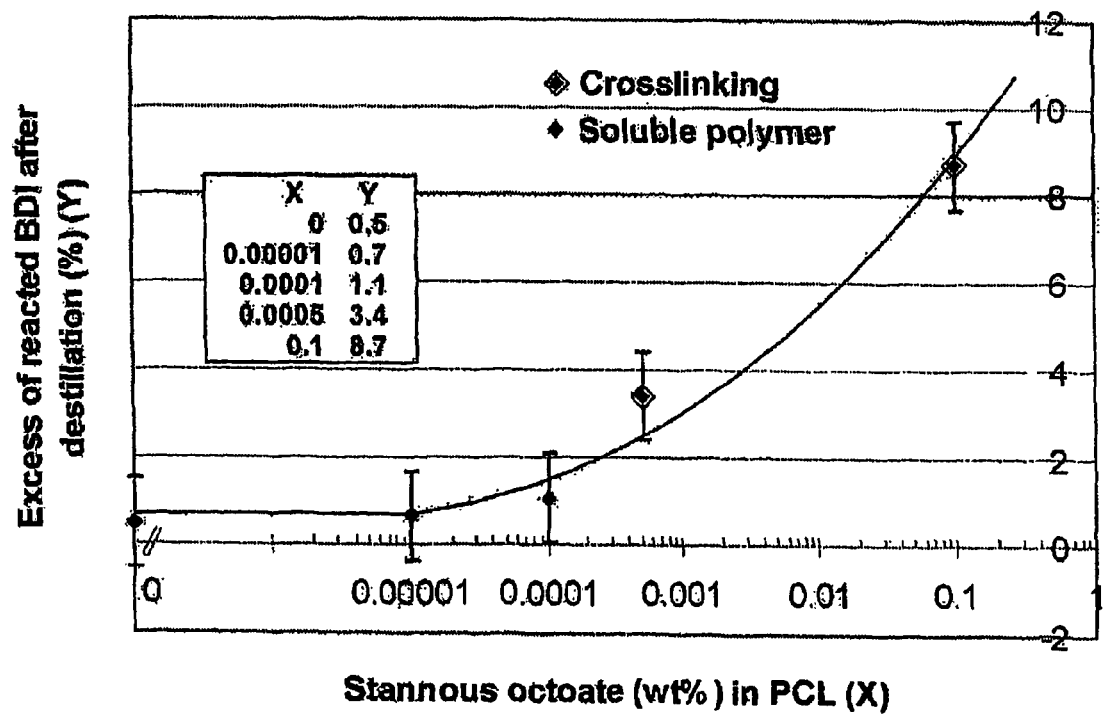

METHOD FOR THE PREPARATION OF NEW SEGMENTED POLYURETHANES WITH HIGH TEAR AND TENSILE STRENGTHS AND METHOD FOR MAKING POROUS SCAFFOLDS

FIELD OF THE INVENTION

This invention relates to the preparation of biomedical materials based on segmented polyester urethanes. The invention also relates to the preparation of foams of these materials. This invention is also related to materials obtainable according to these methods and the use of these materials, e.g. as biomedical materials.

BACKGROUND OF THE INVENTION

Segmented polyurethane elastomers, which are block copolymers consisting of alternating hard (glassy or semi crystalline) and soft (elastomeric) chain segments, have unique physical and mechanical properties and are known to be biocompatible and blood compatible, due to their hard-segment-soft-segment microphase structure (M. D. Lelah and S L Cooper. Polyurethanes in medicine, CRC Press, Boca Raton, Fla., 1986). For these reasons they are used for a number of biomedical applications.

It is known that aromatic polyurethanes possess better mechanical properties than aliphatic polyurethanes. For many biomedical applications, especially in orthopedic applications, like bone replacement, meniscal reconstruction, or spinal disc replacement, good mechanical properties are required because the forces that orthopedic implants undergo are tremendous. For meniscal reconstruction and meniscal replacement with a degradable porous scaffold, the tear strength of the polymer has found to be important for suturing the implant in place and for the stability of the implant until ingrowth of tissue is complete (De Groot et al. Polymer Bulletin, 1997, 38, 211-218).

The use of aromatic polyurethanes for biomedical applications, especially for applications where degradation of the polymer is required, is undesired. It has been shown that polyurethanes release diamines, which originate from the diisocyanate component in the polymer. The diamines that are released upon degradation for commonly used 4,4'-diphenylmethane diisocyanate and toluene diisocyanate based polyurethanes are 4,4'-diaminodiphenylmethane and toluene diamine, respectively, which are known to be very toxic and carcinogenic (M. Szycher. J. Biomaterial Applications, 1988, 3, 297-402).

De Groot et al. (Polymer Bulletin, 1997, 38, 211-218) used a putrescine based diisocyanate, 1,4-butane diisocyanate, for the preparation of poly($\epsilon$-caprolactone) based urethane ureas with excellent mechanical properties, such as a extremely high tear strength. The polyurethanes ureas were made by endcapping a poly($\epsilon$-caprolactone) macrodiol with a large excess of 1,4-butane diisocyanate to provide a suitable macrodiisocyanate. After this reaction, the excess diisocyanate was removed and the macrodiisocyanate was chain extended with 1,4-butanediamine.

It is known that polyurethane ureas possess better mechanical properties than polyurethanes, due to the higher melting temperature. This is due to a better packing of the hard segments as a result of bifurcated hydrogen bonding (L. Born et al. Colloid and Polymer Science, 1985, 263, 355). That is the reason why polyurethane ureas are more difficult to process compared to polyurethanes. In addition, polyurethane ureas are more difficult to produce compared to polyurethanes. Due to the high reactivity between diisocyanates and diamines, large amounts of solvents are needed.

C. J. Spaans et al. (Polymer Bulletin, 41, 131-138, 1998) described that polyurethane urea with poly($\epsilon$-caprolactone) soft segments and butane diisocyanate/butanediamine hard segments shows a high tensile strength, a high modulus and a high resistance to tearing. However, the polymer processing proved to be difficult. When in stead of a diamine in the chain extension step a diol (1,4-butanediol) was used, a processible polyurethane was obtained but the tear and tensile strengths were far less. Even polyurethanes with longer hard segments had a lower tear strength than the polyurethane ureas. (C. J. Spaans, Biomedical Polyurethanes Based On 1,4-Butanediisocyanate: An Exploratory Study. 2000 PhD Thesis ISBN 90-367-1232-7, chapter 3).

The mechanical properties are especially important when the polymers are intended for use in implants. To this end, the polymers are e.g. processed into porous scaffolds used for, for example, tissue engineering, bone replacement, meniscal reconstruction and meniscal replacement.

Spaans et al. attempted to enhance the mechanical properties of the polyurethanes by synthesising polyurethanes with longer hard segments. A chain extender was synthesised from 1,4-butane diisocyanate (BDI) and 1,4-butanediol (BDO) first, and the resulting BDO.BDI.BDO chain extender was subsequently reacted with the macrodiisocyanate (C. J. Spaans et al., Polymer Bulletin, 41, 131-138, 1998). This method with the BDO.BDI.BDO chain extender is also described in WO9964491, wherein a method for the production of polyurethanes based on co-polyesters of caprolactone and L-lactide is described. The BDO.BDI.BDO or BDI.BDO.BDI.BDO.BDI blocks described in WO9964491 were used as chain extenders for a macrodiisocyanate or macrodiol respectively. When the latter block was used, good results were obtained. However, the synthesis of these longer chain extenders complicates the production method.

A need therefore still existed for segmented polyurethane elastomers that are easy to synthesise, have good mechanical properties and can be processed into, for example, porous scaffolds (foams) for use as implants.

The synthesis of polyurethanes is in the state of the art usually carried out in the presence of a catalyst, such as stannous octoate, dibutyl stannous dilaureate and/or tertiary amines, such as diazabicyclooctane.

A process for the preparation of catalyst free polyurethanes is also described in U.S. Pat. No. 5,374,704. In this process macrodiols such as Desmophen 2000 are reacted with a (cyclo)aliphatic diisocyanate and chain extended with a (cyclo) aliphatic diol. The process is a conventional two-step process wherein the pre-polymer is first reacted with the diisocyanate, and subsequently chain extended with the diol. When an excess diisocyanate was used, the excess was not removed. In the chain extent step a larger amount of chain extender was used resulting in larger hard segment. These hard segments are not uniform, which is related to the synthesis process. The minimum temperature required for the chain extension step in the process described in U.S. Pat. No. 5,374,704 is 100° C. Mechanical properties of the resulting polymers described in U.S. Pat. No. 5,374,704 were not tested and were not compared to prior art polymers that were synthesised with a catalyst.

Spaans (C. J. Spaans, Biomedical Polyurethanes Based On: 1,4-Butanediisocyanate: An Exploratory Study. 2000 PhD Thesis ISBN 90-367-1232-7, chapter 2) synthesised polyurtehanes ureas from a macrodiol (poly $\epsilon$-caprolactone), a diisocyanate (butane diisocyanate) and a diamine (1,4 butanediamine).

Spaans compared two different methods for the synthesis of the polyurethane ureas. In a first method, the macrodiol was reacted with 2 equivalent diisocyanate, and subsequently chain extended with a diamine. In a second method, the macrodiol was reacted with an excess of diisocyanate to ensure the formation of a diisocyanate endcapped diol. The excess of diiosocyanate was used to ensure the reaction of each macrodiol with two molecules of diisocyanate (and to prevent the formation of macrodiol dimers, trimers etc linked by isocyanate groups). The excess of diisocyanate was removed prior to chain extension with the diamine. The excess of diisocyanate was removed prior to chain extension to prevent the formation of multimers of the chain extender (linked by diisocyanate groups). By this second method, a small size distribution of hard segments formed in the chain extension step is obtained, resulting in improved mechanical properties, compared to the polyurethanes obtained in the first method (or the method disclosed in U.S. Pat. No. 5,374,704, where a narrow size distribution of hard segments cannot be ensured).

For the second method of Spaans, it is essential that all intermediate reaction steps go to completion, i.e. that all —OH groups on the macrodiol molecules are endcapped, especially since the unreacted diisocyanate is removed from the reaction mixture afterwards. Any remaining unreacted —OH group on a macrodiol molecule, will prevent the subsequent formation of a polyurethane in the chain extension step.

In contrast, in the first method of Spaans (and U.S. Pat. No. 5,374,704) unreacted diisocyanate remains in the reaction mixture and may still react with any remaining —H groups during the chain extension step.

With respect to the preparations of porous scaffolds, several techniques are known in the art. Gogolewski and Pennings (Makro. Rapid Com. 1982, 3, 839; Makro. Rapid com. 1983, 4, 213) used a dipcoat technique, in which a polymer solution is mixed with particulate material. A mandrel is dipped in the polymer solution/particulate, after which the coated mandrel was dipped in a non-solvent for the polymer, which resulted in precipitation of the polymer. Subsequently, the particulate material was washed out. In order to produce porous scaffolds with a reasonable thickness (>1 mm), the method has to be repeated several times, which is a disadvantage.

The preparation of thick porous scaffolds is possible using particulate leaching (e.g. De Groot and Pennings et al., Colloid and Polymer Science, 1990, 268, 1073). The essence to create an open-interconnected-pore structure with this technique is that the particles of the pore forming material have to make contact with each other. This technique has disadvantages. In order to obtain an open interconnected pore structure, large amounts of leaching material are required. This results in high porosity materials with no strength and compression modulus. In addition, it has found to be difficult to leach out all the particulate. The remaining salts in the scaffold can cause cell damage.

Another technique has been described by Aubert et al. to produce low density foams (J. H. Aubert and Clough. Polymer, 1985, 26 2047-2054). Polymer solutions are frozen, after which the solvent is removed by sublimation (freeze-drying). The technique of freeze drying for the removal of the solvent, in stead of precipitation (e.g. Gogolewski and Penning, see above), enables the preparation of thick porous scaffolds. The solid solvent keeps the polymer structure fixated during solvent removal. The morphology of the pores, depends on the phase diagram of the polymer in the particular solvent and the freezing point of the solvent. Pore sizes up to 20 µm are reported, which are too small for tissue engineering applications.

The same technique has also been described as a method to produce biomedical porous polymers (Y. S. Nam and T. G. Park. Biomaterials, 1999; 20, 1783-1790). The resulting porous structures had either pores that were too small (below 30 micrometer) for biomedical applications or were poorly interconnected (interconnection between pores was less than 30 µm).

De Groot et al. (Colloid and Polymer Science, 1990, 268, 1073-1081) combined freeze-drying and particulate leaching. A polymer solution, mixed with particulate material, was frozen. The solvent was removed by sublimation and the NaCl crystals were washed out. The pore structure contained large pores (100-300 µm) due to leaching out of the NaCl crystals and small channel-like pores with diameter<50 µm due to crystallization of the solvent. This technique enables the formation of pores with a specific size. Interconnectivity of the pores is obtained by sublimation of the solvent. By sublimation of the solvent, the polymer structure is stabilized during solvent removal.

A disadvantage of freeze-drying polymer solutions is that it requires solubility of the polymer in solvent that can be freeze-dried. 1,4-Dioxane is the most frequently used solvent to prepare porous materials for tissue engineering. For polymers that are not soluble in the solvents which are applicable for freeze-drying, this technique cannot be used.

A method that does not require solubility in solvents that can be freeze-dried is described in WO9925391. A polymer solution was mixed with particulate material. Then the temperature of the mixture was decreased and after that the mixture was poured into a fluid of a certain temperature that is non-solvent for the polymer and a solvent for the particulate material. A great disadvantage of this method is that the structure is formed during washing and, therefore, the porous structure is not easy to control.

When e.g. meniscus implants are used, it is important that these implants have a high porosity with a high interconnectivity, in order to get a good ingrowth of new tissues, and a high (tear) strength and a high compression modulus to deal with the forces that the implant experiences. To promote ingrowth the interconnection between the pores is preferably more than 30 µm.

Hence, there is also a need for a method for the preparation of porous scaffolds that fulfill these requirements.

Accordingly, the present invention is directed to a method for the preparation of polyurethanes, and a method for producing porous scaffolds (thereof).

SUMMARY OF THE INVENTION

The present invention provides a method for the preparation of a polyurethane wherein a macrodiol, a diisocyanate and a chain extender are used, comprising:
  a) reacting either the macrodiol or the chain extender with an excess of diisocyanate, resulting in a macrodiisocyanate or a reaction product of the diisocyanate and the chain extender, respectively,
  b) removing the remaining unreacted diisocyanate,
  c) reacting the macrodiisocyanate with the chain extender or the macrodiol with the reaction product,
    wherein a) and c) are carried out in the substantial absence of a catalyst.

In a specific embodiment, the present invention provides a method for preparing a polyurethane wherein a macrodiol, a diisocyanate and a chain extender, the chain extender comprising a (cyclo)aliphatic diol, are used, comprising:
a) reacting either the macrodiol or the chain extender with an excess of diisocyanate, resulting in a macrodiisocyanate or a reaction product of the diisocyanate and the chain extender,
b) removing the remaining unreacted diisocyanate,
c) reacting, the macrodiisocyanate with the chain extender or the macrodiol with the reaction product,
wherein a) and c) are carried out in the substantial absence of a catalyst.

The present invention also provides a method for making a porous scaffold from an polymer, e.g. a polyurethane obtainable according to the invention, comprising:
a) providing a homogeneous solution of the polymer in a solvent wherein the polymer-solvent combination is choosen in such a way that for the choosen combination liquid-liquid phase separation occurs, upon cooling down, at a temperature ($T_{liq}$) that is higher than the crystallization temperature of either the polymer ($T_{c,p}$) or the solvent ($T_{c,s}$),
b) adding a particulate material that is insoluble in the solvent,
c) cooling down the mixture obtained at b) at a rate that allows liquid-liquid phase separation to result in the desired micropore morphology for the porous scaffold, to a temperature below the crystallization temperature of either the polymer ($T_{c,p}$) or the solvent ($T_{c,s}$),
d) washing the mixture obtained at c) with a non-solvent, wherein the polymer is insoluble, but wherein the particulate material can be dissolved, at a temperature below the melting temperature of the polymer in solution ($T_{m,p}$), or at a temperature below the melting temperature of the solvent ($T_{m,s}$), for a time sufficient to allow dissolution of the particles of the particulate material.

The invention also comprises porous scaffolds, prepared according to the method of the invention for making porous scaffolds, based on these polyurethanes, or based on other elastomers. Body implants, like meniscus implants, made according to the method of the invention for preparing polyurethanes or porous scaffolds are also comprised in the invention.

SHORT DESCRIPTION OF THE FIGURES

Figure 2:
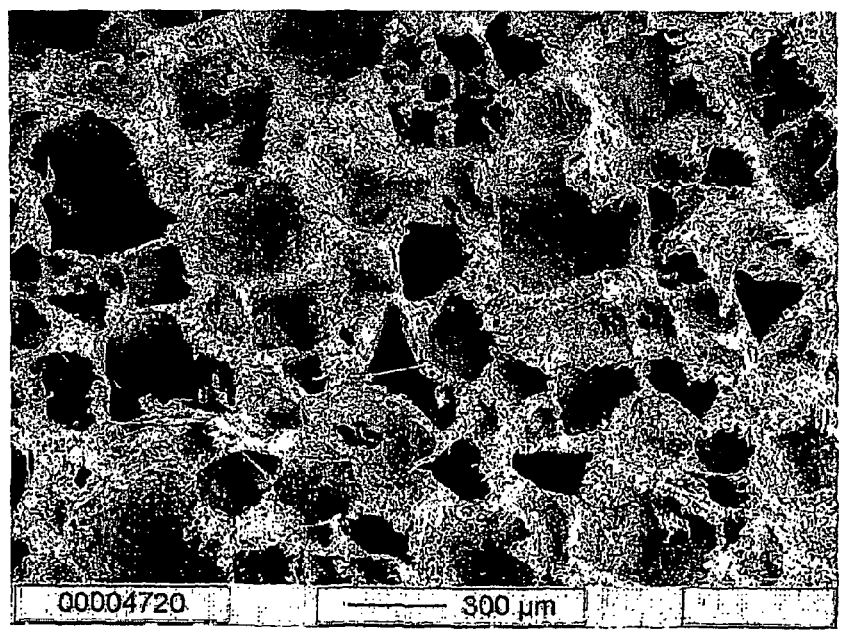
Figure 3:
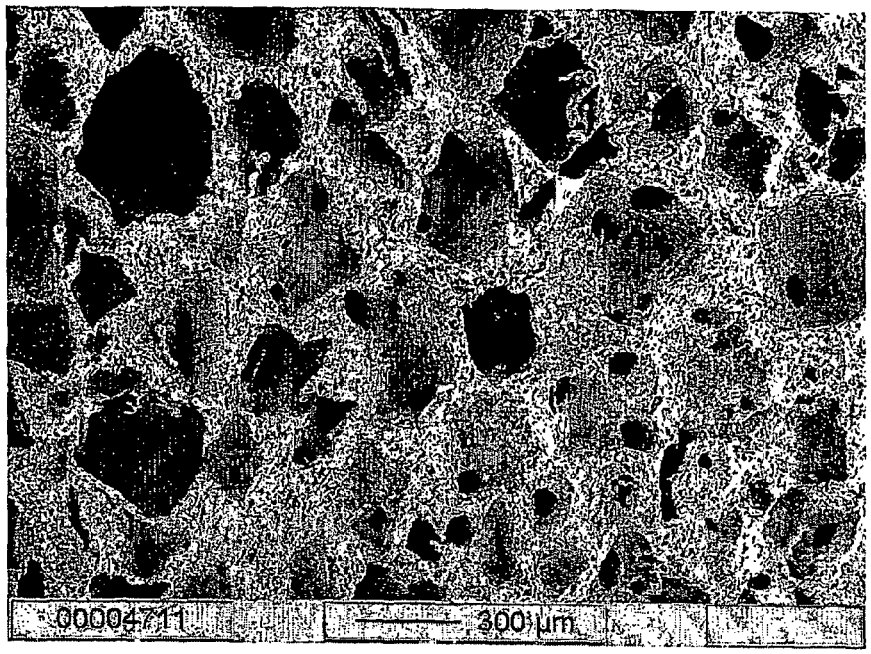
Figure 4:
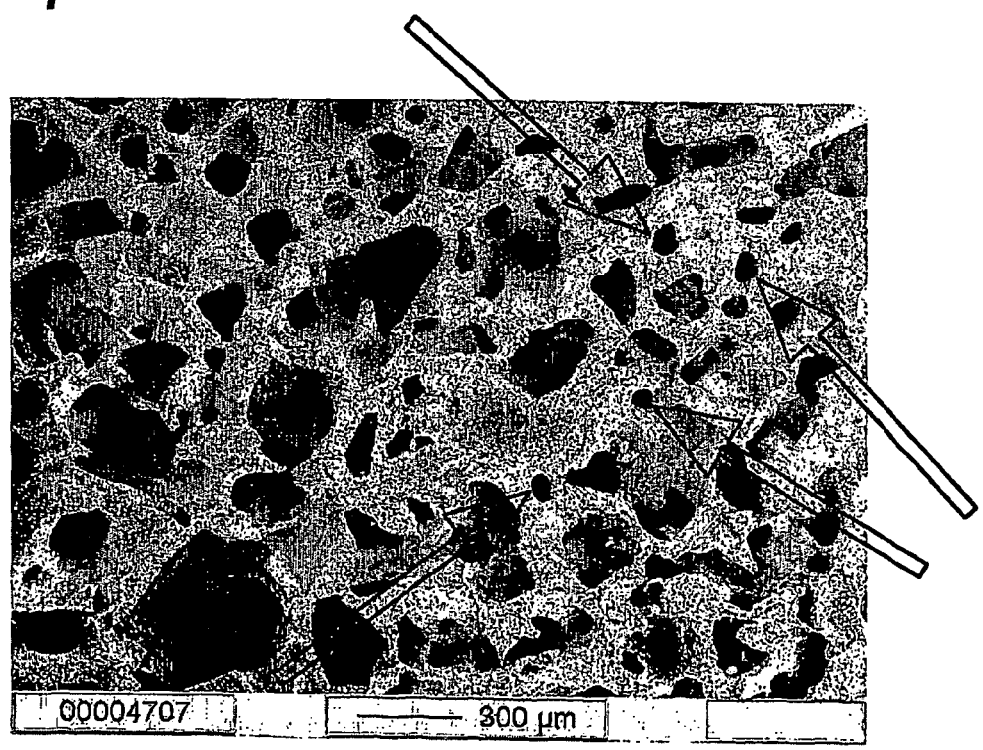
Figure 5:
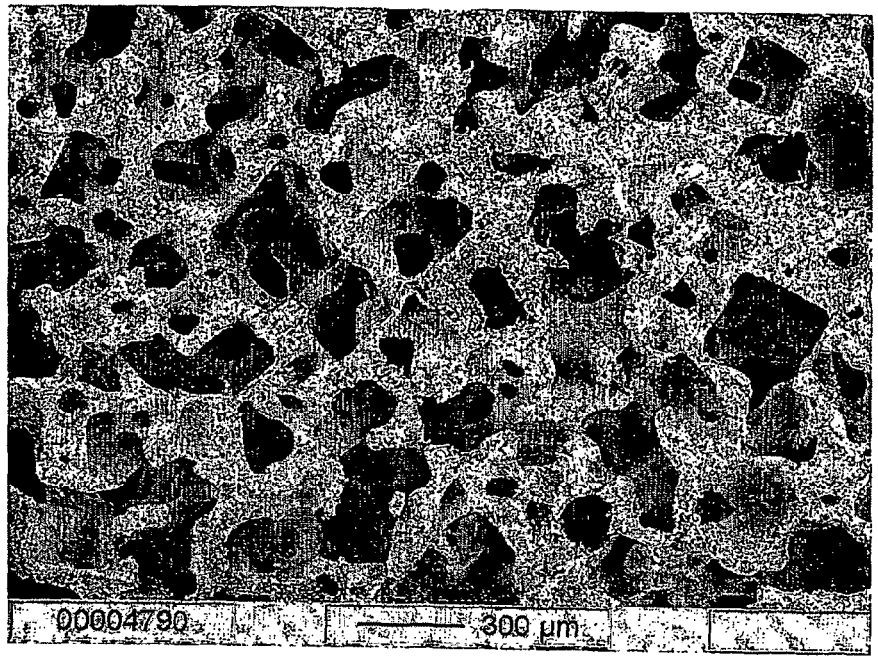
Figure 6:
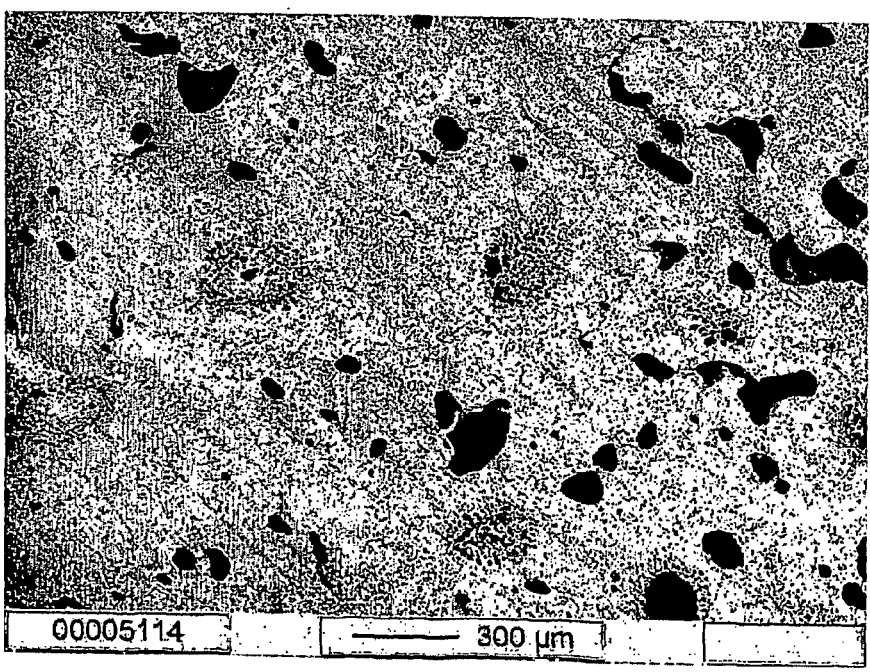
Figure 9:
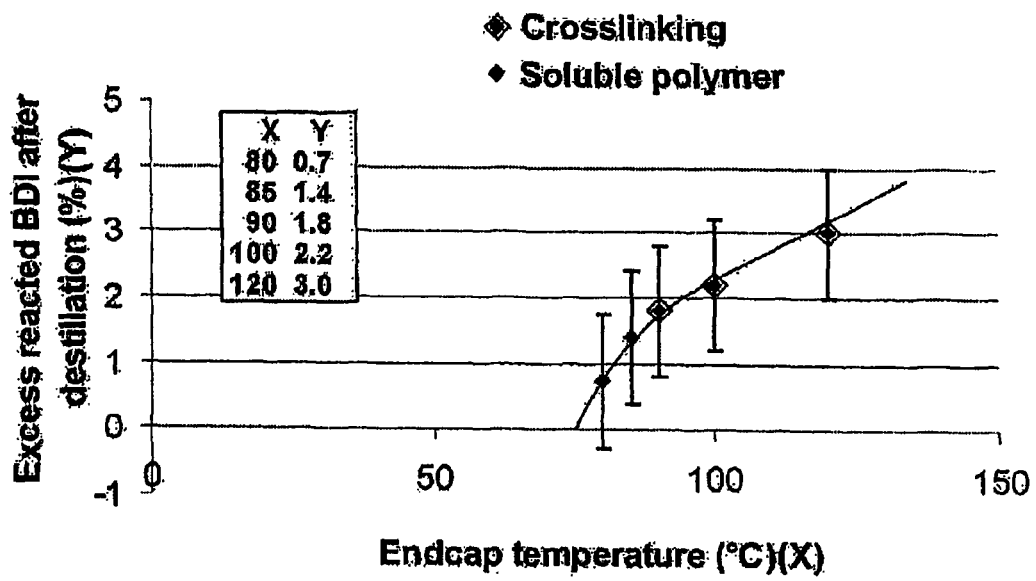
Figure 10A:
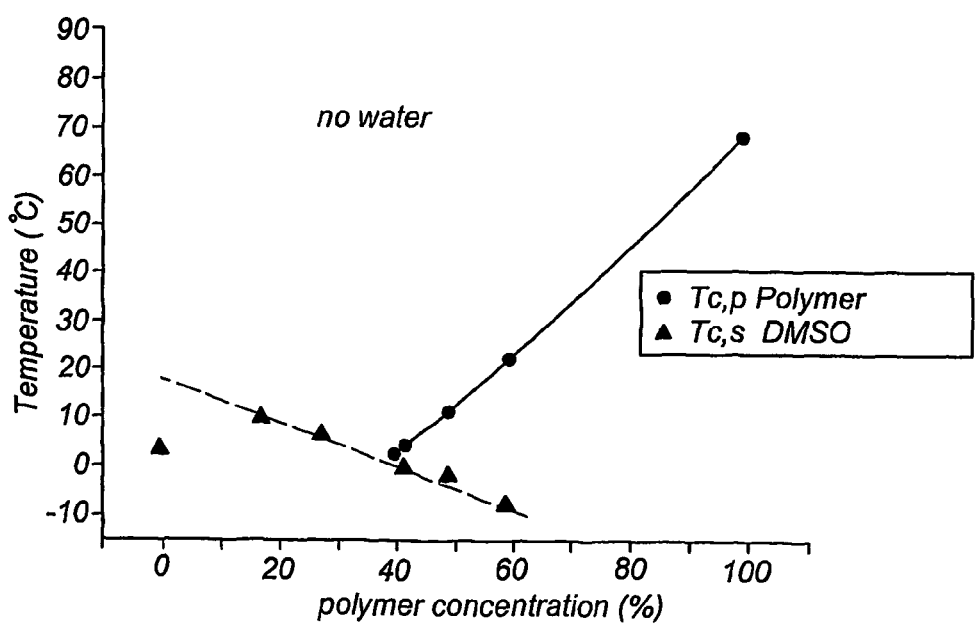
Figure 10B:
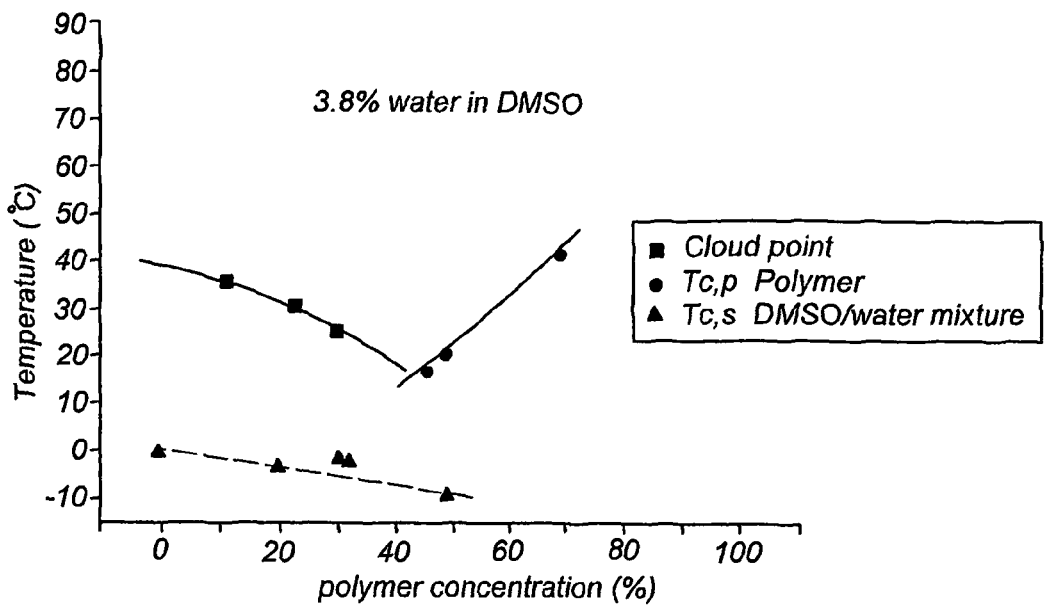
Figure 10C:
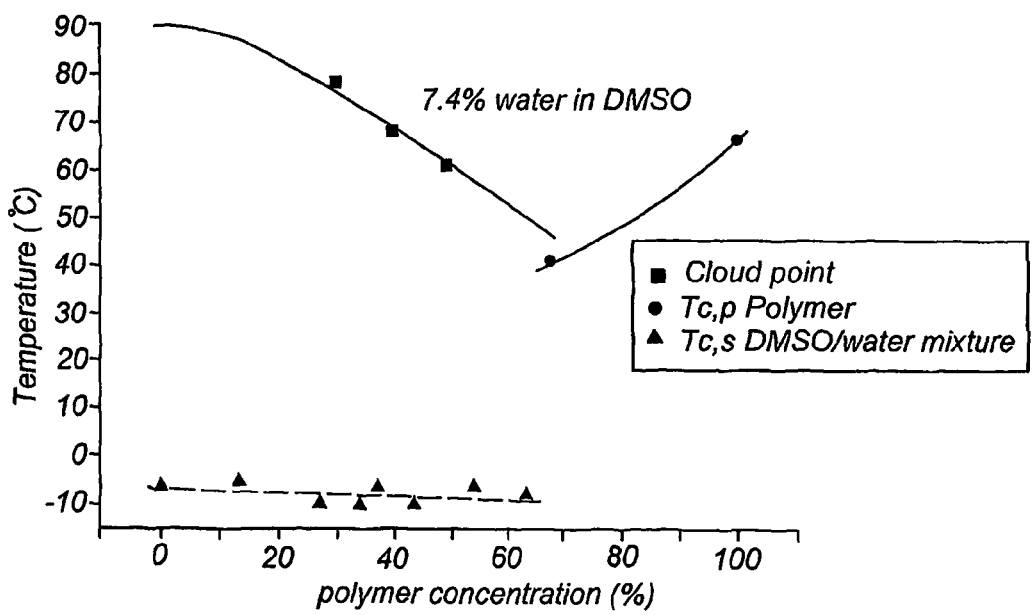
Figure 11:
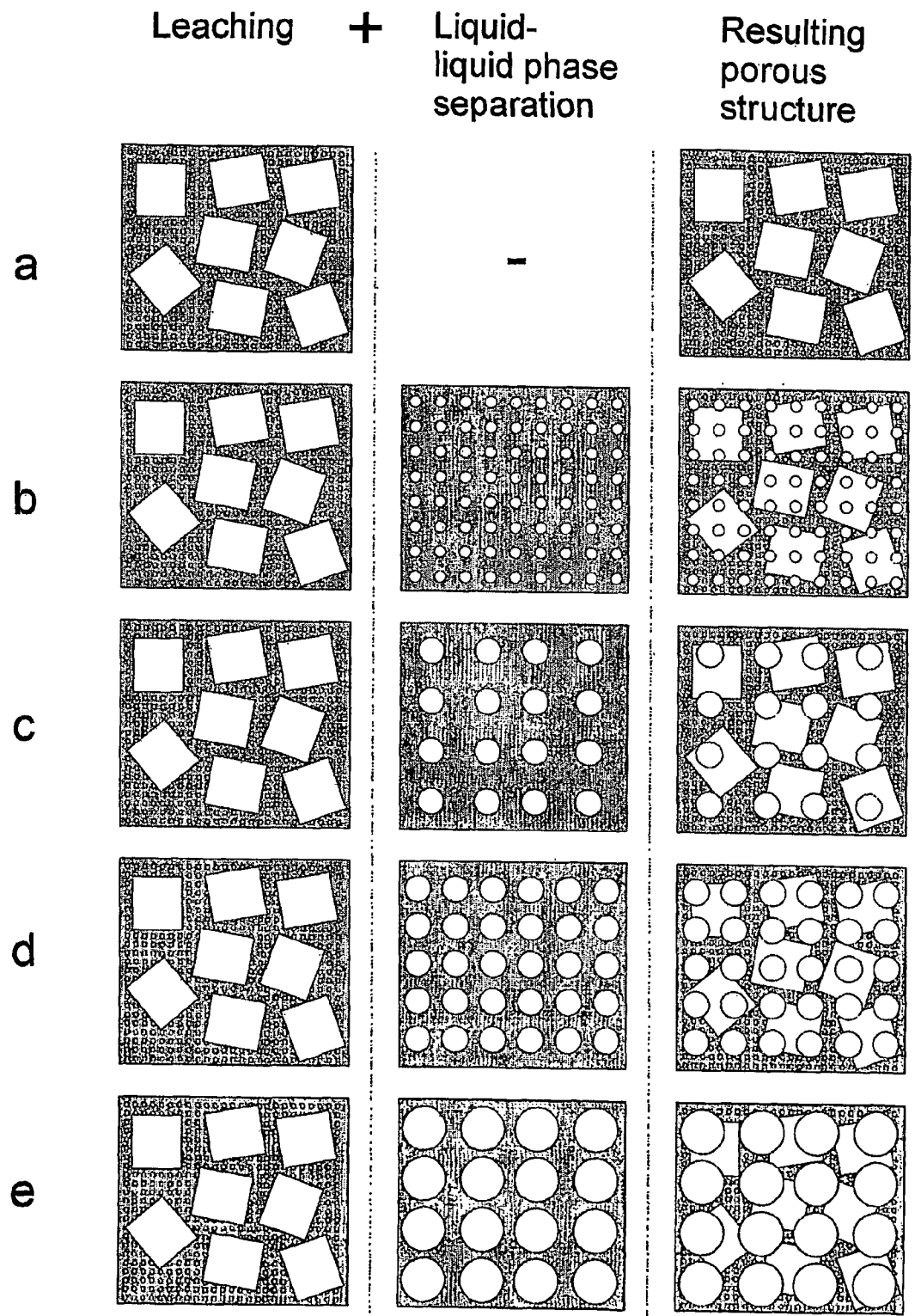

FIG. 1: Example of a phase diagram of a polymer solution.
FIG. 2: SEM photograph of a porous scaffold made according to example 4, based on a polymer synthesised from poly(ε-caprolactone) with a molecular weight of 2000 g/mol, 1,4-butane diisocyanate and 1,4-butanediol, made according to example 1. No water was added to the polymer solution in DMSO.
FIG. 3: SEM photograph of a porous scaffold made according to example 4, based on a polymer synthesised from poly (ε-caprolactone) with a molecular weight of 2000 g/mol, 1,4-butane diisocyanate and 1,4-butanediol, made according to example 1. The percentage water in the solvent was 3.8 wt. %.
FIG. 4: SEM photograph of a porous scaffold made according to example 4, based on a polymer synthesised from poly (ε-caprolactone) with a molecular weight of 2000 g/mol, 1,4-butane diisocyanate and 1,4-butanediol, made according to example 1. The percentage water in the solvent was 6.5 wt. %.
FIG. 5: SEM photograph of a porous scaffold made according to the procedure described in example 4, based on a polymer synthesised from poly(ε-caprolactone) with a molecular weight of 1600 g/mol, 1,4-butane diisocyanate and 1,4-butanediol, made according to example 1. The percentage water in the solvent was 7.4 wt. %.
FIG. 6: SEM photograph of surface of polymer scaffold made according to the procedure described in example 4 (FIG. 4), based on a polymer synthesised from poly(ε-caprolactone) with a molecular weight of 1600 g/mol, 1,4-butane diisocyanate and 1,4-butanediol, made according to example 1. The percentage water in the solvent was 6.5 wt. %.
FIG. 7: SEM photograph of surface of polymer scaffold made according to the procedure described in example 5, based on a polymer synthesised from poly(ε-caprolactone) with a molecular weight of 1600 g/mol, 1,4-butane diisocyanate and 1,4-butanediol, made according to example 1. The percentage water in the solvent was 6.5 wt. %.
FIG. 8: Influence of catalyst concentration on the excess amount of BDI remaining in the macrodiisocyanate after endcapping of poly(ε-caprolactone) as determined by distillation.
FIG. 9: Influence of endcap temperature on the excess amount of BDI remaining in the macrodiisocyanate after endcapping poly(ε-caprolactone) as determined by distillation.
FIG. 10a-c: Examples of different phase diagrams based on the polymer of example 1, solved in DMSO and different amounts of water (a: no water added; b 3.8 wt. % and c 7.4 wt. %).
FIG. 11: Schematic drawing of different porous structures (a-e) after leaching and liquid-liquid phase separation with different liquid-liquid phase separation temperatures with respect to the crystallization temperature $T_{cp}$ and $T_{cs}$.

DESCRIPTION OF THE INVENTION

It has now surprisingly been found that a method wherein the excess of diisocyanate is removed prior to chain extension, can further be improved by removing the catalyst from the process, leading to improved mechanical properties of the resulting polyurethanes.

The melting point and the melting enthalpy of the hard segments of the polyurethanes synthesised with the method according to the invention are increased, and the mechanical properties as tensile strength and tear strength of the polyurethanes synthesised are improved, when compared to prior art methodes (C. J. Spaans, Biomedical Polyurethanes Based On: 1,4-Butanediisocyanate: An Exploratory Study. 2000 PhD Thesis ISBN 90-367-1232-7, chapter 2) where a catalyst was used, and wherein the catalyst was used in a concentration of about 0.08 wt. % (wt. catalyst/wt. polymer).

The present invention provides a method for preparing a polyurethane wherein a macrodiol, a diisocyanate and a chain extender are reacted in a process comprising the steps of:
a) reacting either the macrodiol or the chain extender with an excess of diisocyanate, resulting in a macrodiisocyanate or a reaction product of the diisocyanate and the chain extender
b) removing the remaining unreacted diisocyanate,
c) reacting, the macrodiisocyanate with the chain extender or the macrodiol with the reaction product,
wherein a) and c) are carried out in the substantial absence of a catalyst.

According to this invention, a macrodiol is to be understood as a polymer having terminal hydroxy groups, wherein the polymer has a (number average) molecular weight of about 600 to about 3000 g/mol. Suitable examples and preferred embodiments of the macrodiol are given below.

According to this invention, a diisocyanate is to be understood as a compound having the formula OCN—R—OCN, wherein R is a $C_2$-$C_{14}$ aliphatic or cycloaliphatic radical. preferably a $C_2$-$C_{14}$ alkylene or cycloalkylene radical. If R is an aliphatic radical, it is preferred that the OCN-groups are terminal groups. The aliphatic radicals may be lienar or branched and are preferably linear. More preferably, R is a $C_3$-$C_{12}$ aliphatic or cycloaliphatic radical. Suitable examples and preferred embodiments of the diisocyanates are given below.

According to this invention, a chain extender is to be understood as a compound having the formula Y—R—Y, wherein R is a $C_2$-$C_{14}$ aliphatic or cycloaliphatic radical. preferably a $C_2$-$C_{14}$ alkylene or cycloalkylene radical, and wherein Y represents OH, $NH_2$ or NHR*, wherein R* is a $C_1$-$C_{12}$ aliphatic radical, preferably an alkyl radical. If R is an aliphatic radical, it is preferred that the Y groups are terminal groups. The aliphatic radicals may be linear or branched and are preferably linear. More preferably, R is a $C_3$-$C_{12}$ aliphatic or cycloaliphatic radical. Most preferably, Y is OH. Suitable examples and preferred embodiments of the chain extender are given below.

With "the substantial absence of a catalyst" is meant a catalyst concentration below 0.001 wt.-% (wt. catalyst/wt. polyurethane), preferably below 0.0001 wt.-% and most preferably no catalyst at all. Hence, in an embodiment, the invention is directed to a method for preparing a polyurethane wherein the catalyst concentration is below 0.001 wt.-% (wt. catalyst/wt. polyurethane).

The polyurethanes made according to process of the invention have different thermal properties and better mechanical properties than the polyurethanes made according the same process but made with a catalyst. With the method of the invention the chain extension may even be carried out at temperatures as low as 80° C.

The method for preparing polyurethanes according to the invention may involve reaction of either a macrodiol or a chain extender with an excess of diisocyanate, after which the remaining unreacted diisocyanate is removed. The reaction of a macrodiol with a diisocyanate results in a macrodiisocyanate (a macrodiol that has been "end-capped" with a diisocyanate) that can be reacted with a chain extender (usually a diol or diamine) to form a polyurethane or polyurethane urea, after the remaining unreacted diisocyanate has been removed.

Alternatively, the chain extender (such as a diol or diamine) may be reacted with the diisocyanate, resulting in a reaction product of the chain extender and the diisocyanate. This reaction product, a chain extender that has been "end-capped" with the diisocyanate, can, after the remaining unreacted diisocyanate has been removed, be reacted with the macrodiol to form a polyurethane. In both embodiments of the method of the invention a polyurethane with the same repeating unit is obtained.

In an embodiment, step a, the endcap step (a) of either the macrodiol or the chain extender, is carried out at a temperature between about 50-120° C., e.g. between about 50-100° C. or preferably between about 50-90° C. In a further preferred embodiment, the temperature is between about 60-85° C.

Preferably the method for the preparation of a polyurethane according to the invention comprising the steps of reacting the macrodiol with an excess of a diisocyanate to obtain a macrodiisocyanate, and then the subsequent steps b) removing the remaining unreacted diisocyanate, and c) reacting the macrodiisocyanate with a chain extender.

The method of the invention results in polyurethanes that have excellent mechanical properties and can e.g. be processed into foams for use as porous scaffolds in body implants.

The macrodiol used in the method according to the invention may be a known polyether and copolyethers based on, for example, tetrahydrofyran, ethyleneoxide or propyleneoxide; polyesters and copolyesters made by polycondensation based on, for example, adipic acid and diols or hydroxyacids, such as lactic acid; polyesters and copolyesters made by ringopening polymerization, based on, for example, ε-caprolactone, lactide, glycolide, δ-valerolactone, 1,4-dioxane-2-one, 1,5-dioxepan-2-one, oxepan-2,7-dione; polycarbonates and copolycarbonates based on, for example 1,6-hexanediol polycarbonate; polycarbonates and copolycarbonates made by ringopening polymerization based on, for example, trimethylenecarbonate (1,3-dioxane-2-one), 1,3-dioxepan-2-one or 1,3,8,10-tetraoxacyclotetradecane; polymers and copolymers based on combinations of above described components; polymers made ringopening polymerizarion are preferred. Also combinations of macrodiols can be used.

Preferred macrodiols are the ones that are made by ring opening polymerization Good results were obtained when poly(ε-caprolactone)diol was used as macrodiol. Preferably, a poly(ε-caprolactone) with a molecular weight between 600 and 3000 g/mol, more preferably between 1000-2200 g/mol, was used.

The reaction to form the macrodiol can be carried out in accordance with procedures which are known in polyurethane chemistry. Macrodiols made by ring opening polymerization are normally synthesised in the presence of a catalyst (e.g. stannous octoate, dibutyl stannous laurate). With the method of the invention, the macrodiol may be synthesised catalyst-free. The advantage of such a method is that the catalyst does not need to be removed after the macrodiol is synthesised. Thus, for example, a macrodiol such as poly(ε-caprolactone), which is produced by ring opening polymerization, is preferably produced in a catalyst-free method, when it is used in the method of the invention.

In the production of polyurethanes many different diisocyanates, both aromatic and aliphatic, have been used. However, when the resulting polyurethanes are intended for use in biomedical applications aliphatic or cycloaliphatic diisocyanates are preferred. Aliphatic diisocyanates for use in the method of the invention include, for example, the known aliphatic and cycloaliphatic diisocyanates such as, for example 4,4'-dicyclohexanemethane (H12MDI or reduced MDI), 1,4-transcyclohexane-diisocyanate (CHDI), isophorone diisocyanate (IPDI), 1,6-hexane diisocyanate (HDI) or 1,4-butane diisocyanate (BDI).

An excess diisocyanate is used to diminish the risk of the formation of macrodiol dimers (two polyols combined with one diisocyanate) and trimers (three macrodiols combined with two diisocyanates). With an excess of diisocyanate is meant a ratio at least above 2:1 (diisocyanate:macrodiol). Preferably the ratio is above 6:1, most prefererably above 8:1. When a polycaprolacton macrodiol and butane diisocyanate were used, good results were obtained when the ratio BDI: polycaprolacton diol was 9:1.

Reaction between macrodiol and diisocyanate take place at usual temperatures of about 80° C. (Thermoplastic Elastomers, A comprehensive Review. Ed N. R. Legge, G. Holden, H. E. Schroeder. Hanser Publishers, Munich 1987). When no solvent is added, the reaction can take place between 50° C.-120° C. In an embodiment, step c, the chain extension step, is carried out at a temperature between about 50-180° C., e.g. between about 50-120° C. or preferably between about 50-100° C. In solution, a higher temperature can be chosen, e.g. 80° C.-150° C., which depends on the concentration. For example, when in the bulk polymerization is performed at 80° C., and results in polymer with sufficient molecular weight, it was found that in solution at a concentration of 50%, at a temperature of 80° C., the resulting polymer had a lower molecular weight. Either the temperature or the concentration of the polymer in the solvent can be raised to obtain good results. These temperatures are especially applicable for the preparation of polyurethanes wherein the chain extender is a diol. When the chain extender is a diamine, and polyurethane ureas are made, lower temperatures may be used like e.g. room temperature. Preferably, chain extension takes place in the substantial absence of a solvent (bulk).

After the reaction of the diisocyanate with either the macrodiol or the chain extender has been completed, removal of the unreacted diisocyanate can be done by evaporation under reduced pressure or by extraction. When the diisocyanate is removed by evaporation, the amount diisocyanate that is removed can be determined by weighing or by spectroscopic techniques like NMR and IR. Extraction can be performed using for instance a soxlet apparatus.

It is important that the extraction medium is free of traces of water and that the unreacted diisocyanate dissolves and the macrodiisocyanate does not dissolve in the extraction medium. When for instance 1,4-butane diisocyanate and polycaprolactone are used for the macrodiisocyanate, hexane can be used as extraction medium.

Suitable chain extenders include diol and diamine compounds. Suitable diamines include aliphatic diamines including ethylene-, propylene-, butane-, and hexamethylenediamines; cycloaliphatic diamines, such as, for example 1,4-isophorone diamine and 1,4-cyclohexane diamine. Another example of a suitable diamine is 1,4 butanediamine. Hence, the invention is also directed to a method wherein the chain extender comprises a diamine. The diamines can e.g. be selected from the group consisting of ethylene-, propylene, butane-, hexamethylene-diamines, like 1,2-ethylene diamine, 1,6-hexamethylene diamine etc., 1,4-isophorone diamine, 1,4-cyclohexane diamine and 1,4-cyclohexane diamine, etc.

The use of a diamine usually results in polyurethane ureas with better mechanical properties, compared to polyurethanes based on a diol chain extender. However, it has been found that with the method of the invention polyurethanes can be synthesized with excellent mechanical properties. The mechanical properties of polyurethanes prepared according to the method of the invention are comparable to those of state of the art polyurethanes ureas, The use of a diol as chain extender instead of a diamine has the advantage that the method parameters are easier to control and the produced polyurethane is easier to method. The use of a diol as chain extender in the method of the invention is therefore preferred.

Suitable diols for use as a chain extender in the method of the invention may be (cyclo) aliphatic diols such as for example ethyleneglycol, diethylene glycol, dipropylene glycol, 1,4-butanediol (BDO), 1,6-hexanediol (HDO), 1,8-octanediol, neopentyl glycol, 1,12-dodecanediol, cyclohexanedimethanol, or 1,4-cyclohexanediol.

Preferably, when for example, BDI is used as the diisocyanate, BDO is used as the chain extender.

When BDO was used with the method of the invention, polyurethanes with excellent mechanical properties were obtained. Aliphatic diols such as 1,4-butanediol or 1,6-hexanediol, when used in the method of the invention, already give polyurethanes with good mechanical properties.

In another embodiment of the method of the invention "diol block" chain extenders may be used. Such "diol blocks" have been described by Spaans et al. (Polymer Bulletin, 41, 131-138, 1998). Diol block chain extenders are reaction products of a diisocyanate and an excess of a diol. Such "diol blocks" may be prepared by reacting a diisocyanate and a diol, after which the unreacted excess diol is removed by for instance evaporation or extraction. Such diol blocks may be, for example, the reaction product of 1,4-butane diisocyanate (BDI) and 1,4-butanediol (BDO) or BDI and 1,6-hexanediol (HDO) or 1,6-hexanediisocyanate (HDI) and HDO, resulting in "diol block" chain extenders like BDO.BDI.BDO, or HDO.HDI.HDO. For the method according to the invention, such "diol block" chain extenders are preferably produced in the absence of a catalyst. Hence, according to this embodiment, the invention is also directed to a method wherein the chain extender is a reaction product of two diisocyanate molecules and one diol molecule (like 1,4 butane diol and 1,4 butane diisocyanate: BDI-BDO-BDI).

Alternatively, the macrodiol may be reacted with a reaction product of a diol or diamine with an excess of diisocyanate. The remaining unreacted diisocyanate is removed by evaporation or extraction. The reaction product may be, for example a reaction product of BDO and BDI (BDI-BDO-BDI) or BDO and HDI (HDI-BDO-HDI) or HDO and BDI (BDI-HDO-BDI) or HDO and HDI (HDI-HDO-HDI), or combinations thereof. The reaction product (diisocyanate compound) can also be the reaction product of a "diol block" and a diisocyanate, resulting in, for example, BDI-BDO-BDI-BDO-BDI or HDI-HDO-HDI-HDO-HDI etc. Hence, according to this embodiment, the invention is also directed to a method wherein the chain extender is a reaction product of two diol molecules and one diisocyanate molecule (like 1,4 butane diol and 1,4 butane diisocyanate: BDO-BDI-BDO).

In both above described embodiments, the chain extender can also comprise more repeating units, like BDO-(BDI-BDO)$_n$ and BDI-(BDO-BDI)$_n$ respectively, wherein n =0-10, e.g. n=1, 2 or 3.

The reaction between the macrodiisocyanate and the chain extender, or, in the alternative, the reaction between the macrodiol and the reaction product of the chain extender and a diisocyanate, can be carried out in accordance with procedures which are well known in polyurethane chemistry. In general the reaction is carried out in the absence of a solvent at temperatures of 80° C.-180° C., and preferably 80-150° C. However, it is possible to carry out the reaction in a solvent such as dimethylesulfoxide (DMSO), dimethylformamide (DMF), chloroform, 1,4-dioxane, N-methylpyrrolidone (NMP), m-cresol. In that case, when using a solvent, higher minimal temperatures are needed (at least 100° C.), and preferably 120° C.

In preparation methods according to the invention the reaction is ended by for example lowering the temperature, when the intrinsic viscosity is at least above 0.7 dl/g, preferably above 0.8 dl/g and most preferably above 0.9 dl/g, in order to have the optimal mechanical properties. Higher intrinsic viscosities are obtained at longer reaction times. It may be that the intrinsic viscosity of the polymer increases during processing of the polymer (e.g. polymer film or porous polymer) but that does not negatively influence the characteristics. In case the intrinsic viscosity is increasing when processing, the reaction can be ended earlier. Good results were obtained when the reaction time was e.g. 16 hours.

The intrinsic viscosity determination is described in any general Polymer Chemistry textbook (e.g. J. M. G. Cowie. Polymers: Chemistry & Physics of modern materials. Second edition. Chapman & Hall, 1991, page 207-209). The mechanical properties as tear strength and tensile strength are a function of the intrinsic viscosity (see example 3).

In an embodiment, the invention is directed to a method wherein the macrodiol has a molecular weight between 1000 and 3000 g/mol, e.g. between 1200-2600 g/mol. For e.g. meniscus implants, scaffolds based on macrodiols having a molecular weight preferably between 1400 and 2200 g/mol, like e.g. 1500-1700 g/mol gave good results.

In one embodiment, the invention provides a polyurethane based on a poly(ϵ-caprolactone) diol with a molecular weight of approximately 1900-2200 g/mol, 1,4-butanediisocyanate and 1,4-butanediol as a chain extender, having a tear strength above 90 kJ/m$^2$, obtainable by the method according to the invention. In another embodiment, the invention provides a polyurethane based on a poly(ϵ-caprolactone) diol with a molecular weight of approximately 1500-1700 g/mol, 1,4-butanediisocyanate and 1,4-butanediol as a chain extender, having a tear strength above 130 kJ/m$^2$, obtainable by the method according to the invention. The person skilled in the art understands that the molecular weights are mean molecular weights.

The invention is also directed to methods wherein the macrodiol comprises e.g polytetramethylene carbonate or polylactide.

The polymers according the invention, have unlike e.g. those of U.S. Pat. No. 5,374,704 more uniform hard segments, since the method of addition of an excess isocyanate, after which the excess is removed, is used. Polymers according to the invention with longer hard segments can be made by repeating the method addition of excess and removal of excess after reaction (as described above). Polymers according to the invention, with good mechanical properties and high molecular weights can also be made below 100° C.

The polyurethane according to the invention is, due to the properties like tensile and tear strengths and the absence of catalyst traces, very suitable for use in biomedical applications.

Provided the polyurethanes can be processed into foams, they can, for example, be used as porous scaffolds used in tissue engineering, as prosthesis or implants, e.g. meniscus reconstructions or replacements. The advantage of porous implants is that the growth of tissue is possible within the pores. To promote the growth of tissue, the porous scaffolds preferably have an interconnected porous structure that may be created by particulate leaching. The diameter of the interconnection between the pores is preferable more than 30 μm.

In general, foams for use as porous scaffolds in body implants can be made in various ways known in the art, such as freeze-drying/particulate leaching. These techniques usually include a step in which the polymer is dissolved in an appropriate solvent and the addition of a non-solvent (in which the polymer does not dissolve) and the addition of a particulate material, usually a crystalline material such as a salt, as pore former. It is essential that the particulate material does not dissolve in the solvent and non-solvent used. The porosity and the structure of the porous scaffold is determined by the concentration of the polymer in the solution and of the amount and particle size of the particulate material added.

Thus a porous scaffold comprising a polyurethane (prepared by the method) according to the invention is likewise part of the present invention. The porous scaffolds may be used as body implants for, for example, meniscus reconstruction or replacement. Such an implant is therefore likewise part of the present invention.

A novel method to prepare porous scaffolds is also part of the invention. This method can be used for the polyurethanes prepared according to the invention, but can also be applied to other elastomers.

This method provides a controllable and reproducible way of making a porous scaffold from an elastomer that is especially suitable for use with the polyurethanes (produced by the method) according to the invention. However, the method for making a porous scaffold according to the invention may likewise be applied to other elastomers suitable for the desired application. The method of the invention results in a porous scaffold, the porosity of which is determined by the combined effects of particulate leaching and phase separation occurring in a solution of the polymer in an appropriate solvent. Especially for polyurtehanes made according to the method of the invention and also for, for example polyurethane ureas, the methods for preparing porous scaffolds of the prior art do not result in an interconnected pore structure that allows ingrowth of cells. When e.g. the technique according to WO9925391 was used for polymers made according to the invention, polymer scaffolds with poorly interconnected pore structures were obtained.

The method for making a porous scaffold according to the invention is based on the finding that a porous scaffold with excellent properties can be obtained when a solution is used wherein, upon cooling down, liquid-liquid phase separation occurs (at a temperature $T_{liq}$, see FIG. 1), prior to crystallization of either the polymer (at the crystallization temperature, $T_{c,p}$, of the elastomer) or the solvent (or solvent/non-solvent mixture) (at the crystallization temperature, $T_{c,s}$, of the solvent (or solvent/non-solvent mixture). Because phase separation occurs prior to crystallization, a very good porous structure is obtained that is fixed (stabilized) when either the polymer or the solvent crystallizes.

The method of the invention is especially suitable for use with polymers that crystallize in solution.

The present invention therefore provides for a method for making a porous scaffold from a polymer, comprising the steps of:

a) providing a homogeneous solution of the polymer in a solvent wherein the polymer-solvent combination is choosen in such a way that for the choosen combination liquid-liquid phase separation occurs, upon cooling down, at a temperature ($T_{liq}$) that is higher than the crystallization temperature of either the polymer ($T_{c,p}$) or the solvent ($T_{c,s}$).

b) adding a particulate material that is insoluble in the solvent, c) cooling down the mixture obtained at b) at a rate that allows liquid-liquid phase separation to result in the desired micropore morphology for the porous scaffold, to a temperature below the crystallization temperature of either the polymer ($T_{c,p}$) or the solvent ($T_{c,s}$)

d) washing the mixture obtained at c) with a non-solvent, wherein the polymer is insoluble, but wherein the particulate material can be dissolved, at a temperature below the melting temperature of the polymer in solution ($T_{m,p}$), or at a temperature below the melting temperature of the solvent ($T_{m,s}$), for a time sufficient to allow dissolution of the particles of the particulate material.

According to the invention, the invention is also directed to a method for making a porous scaffold from a polymer, comprising the steps of:

a) preparing a homogeneous solution of a polymer and a solvent;

b) adding a pore forming material to the homogeneous solution that is not soluble in the solvent to form a homogeneous mixture of the polymer, the solvent and the pore forming material;

c) cooling the homogeneous mixture to a temperature $T_{liq}$ to form a liquid mixture comprising a polymer rich phase and a polymer pore phase, wherein $T_{liq}$ is higher than $T_{c,p}$ and higher than $T_{c,s}$;

d) further cooling the liquid mixture to a temperature below $T_{c,p}$ to form the porous scaffold; and e) washing the porous scaffold with a non-solvent at a temperature T, wherein the T is lower than $T_{m,p}$ or lower than $T_{m,s}$.

In a preferred embodiment, especially with respect to applications as meniscus, etc., the polymer that is used comprises an elastomer, or combinations of elastomers. The polymers (in general), or the elastomers, that can be used in the methods for making a porous scaffold according to the invention are those polymers, that can be solved in a solvent.

In a further preffered embodiment, the methods for making a porous scaffold according to the invention are directed to polyurethanes or polyurethane ureas (elastomeric or not), that are obtainable according to the method for preparing a polyurethane according to the invention.

It is necessary that liquid-liquid phase separation occurs before the polymer in solution crystallize or before the solvent (mixture of solvents and non-solvents) crystallizes. When the temperature at which the polymer in solution crystallizes is higher than the crystallization temperature of the solvent, it is important that $T_{liq} > T_{c,p}$. When the temperature at which the polymer in solution crystallizes is lower than the crystallization temperature of the solvent, it is important that $T_{liq} > T_{c,s}$. This is because at either $T_{c,p}$ or $T_{c,s}$ the structure is fixed and that upon washing in a non-solvent for the polymer, the structure does not change anymore. It is therefore, important that liquid-liquid phase separation occurs before the structure is fixed, which can either be a result of crystallization of the polymer in solution of crystallization of the solvent.

This method advantageously provides porous scaffolds, that can e.g. be used as body implants like meniscus implants, spinal disc implants, etc. The scaffolds have a good porosity and a high interconnectivity, thereby enabling tissue ingrowth, a high (tear) strength and a high compression modulus to deal with the forces that the implant experiences.

Depending upon the kind of elastomer-solvent combination, providing a homogeneous solution of the elastomer in a solvent according to the invention may also include a heating of the solution of the elastomer in a solvent to a temperature above liquid-liquid phase separation.

Preferably, elastomers are used that are capable of crystallization in solution. Thus, preferably a method is used whereby $T_{liq}$ is higher than $T_{c,p}$. If the elastomer does not crystallize in solution, the solution can be cooled till below the crystallization temperature of the solvent.

The interrelation between $C_B$, ($C_B$ being the concentration of a particular elastomer in solution, for which the temperature at which liquid-liquid phase separation occurs ($T_{liq}$) is equal to the crystallization temperature of the polymer in solution ($T_{c,p}$)) $T_{liq}$, $T_{c,p}$ etc. for a solution of a particular polymer in a particular solvent is shown in FIG. 1 (phase diagram). In FIG. 1, a phase diagram of a polymer solution is shown. Such diagram is well known and is described in any polymer textbook on polymer solutions. The phase separation is represented by the binodal. For combinations of temperature and polymer concentrations under the diagram, phase separation occurs.

In addition, the phase diagram shows a melting curve indicated with $T_{m,p}$, representing the melting temperature of the polymer in solution at a certain polymer concentration. The corresponding crystallization curve is also shown and is indicated with $T_{c,p}$, representing the crystallization temperature of the polymer in solution at a certain polymer concentration. (The crystallization of a polymer in solution generally takes place 20-30° C. below the melting point of the polymer in solution).

The arrow in FIG. 1 correspond to a cooling procedure. At higher temperature the polymer solution with a certain polymer concentration ($C_{sol}$) is homogeneous. Upon cooling down, the temperature where the polymer solution starts to phase separate, $T_{liq}$, is reached.

When phase separation occurs the homogeneous solution separates into two liquid phases, a polymer rich phase and a polymer poor phase (together referred to as "polymer diluent" since formally the polymer solution no longer exists). The polymer poor phase contains almost no polymer. Upon further cooling down the concentration of the polymer in the polymer rich phase increases, while the percentage polymer poor phase of the total diluent increases. Thus, in the phase diagram, the concentration polymer in the polymer rich phase, is indicated for each temperature by the binodal. At temperature $T_{c,p}$ the concentration of the polymer in the polymer rich phase has reached the value of $C_B$. Since $T_{c,p}$ is the crystallization temperature of the polymer in solution the polymer crystallizes at this temperature, and prevents further phase separation when the temperature is lowered further below $T_{c,p}$. At this point the volume percentage polymer poor phase is 100×c/(a+c), and the percentage polymer rich phase is 100×a/(a+c).

According to the method, first a homogeneous polymer solution has to be made, which may include a heating step. The solution should have a concentration of the elastomer (polymer) between $0.4C_B$ and $0.9C_B$, preferably between $0.4 C_B$ and $0.8 C_B$. $C_B$ is the concentration of a particular elastomer in solution, for which the temperature at which liquid-liquid phase separation occurs ($T_{liq}$) is equal to the crystallization temperature of the polymer in solution ($T_{cp}$).

If the concentration of the polymer solution that is cooled is between $0.4C_B$ and $0.9C_B$, than the volume percentage of the polymer poor phase is 40-90% of the total volume. The percentage polymer poor phase is related to the pore structure of the final porous scaffold. After the polymer has crystallized and the structure is fixed, the solvent is removed in step d) of the process.

The space that used to be occupied by the polymer poor phase, has formed pores, after the solvent has been washed out of the scaffold.

The morphology of the porous structures of the invention is a combination of pores caused by leaching of the leaching material and liquid-liquid phase separation. In FIG. 11, resulting porous structures under different circumstances are shown. When no liquid-liquid phase separation occurs before $T_{c,p}$ or $T_{c,s}$, the structure contains pores caused by leaching of the leaching material and small pores caused by the solvent (FIG. 11:a). When Liquid-liquid phase separation does occur and $T_{liq} > T_{c,p}$ (or $T_{c,s}$) and the polymer mixture is cooled down relatively fast, the resulting structure contains pores caused by leaching of the leaching material, pores caused by the solvent and pores caused by the liquid-liquid phase separation (FIG. 11:b). The latter pores are spherical like pores. When the same mixture is cooled down relatively slowly, the polymer poor phase that is responsible for the spherical (liquid-liquid phase separation) pores, have time to become bigger. The total amount of polymer poor phase is equal to situation (b) and thus results is fewer larger spherical pores (FIG. 11:c). When $T_{liq} \gg T_{c,p}$ (or $T_{c,s}$) the percentage of polymer poor phase increases, which results in more spherical (liquid-liquid phase separation) pores (FIG. 11:d). When the polymer solution is cooled more slowly, it results in less but bigger spherical (liquid-liquid phase separation) pores (FIG. 11:e).

It has been found that if the concentration of the polymer is lower than 0.4 $C_B$ or higher than 0.9 $C_B$ results in either relatively worse mechanical properties and/or poorer interconnection of the pores of the scaffold.

After a homogeneous polymer solution is made, the polymer solution has to be homogeneously mixed with a pore forming material (particulate material). Suitable pore forming materials are for example saccharose, NaCl. The pore forming material can be sieved to specific sizes (30-1500 μm). It is important that the pore forming material does not dissolve in the solvent. For e.g. meniscus implants, the pore forming material may comprise particles with about 50-700 μm, for example about 100-300 μm.

For the method of the invention it is essential that the solution shows, upon cooling down, liquid-liquid phase separation before the polymer (or the solvent) crystallizes. Thus, liquid-liquid phase separation should occur at a temperature above the crystallization temperature ($T_{cp}$) of the elastomer.

Hence, an appropriate solvent-elastomer combination should be chosen. The conditions and the temperature at which liquid-liquid phase separation occurs can be manipulated by, for example, the addition of an appropriate amount of non-solvent to the solution, and/or by changing the molecular weight and composition of the polymer. When a non-solvent is added, liquid-liquid phase separation will occur at a higher temperature.

By choosing the appropriate conditions, the window in which liquid-liquid phase separation occurs can be influenced for a particular elastomer solution.

The melting point of the polymer as well as melting point of the polymer in solution can be determined by Differential Scanning Calorimetry (DSC) which is a well known technique in Polymer Technology.

For any given polymer/solvent combination (including elastomer/solvent combinations) the temperature at which liquid-liquid phase separation occurs ($T_{liq}$) can be determined by light based techniques, for example light scattering and optical microscopy, methods known to the person skilled in the art or by modultated DSC (M. Reading, B. K. Hanhn, B. S. Crowe, U.S. Pat. No. 5,224,775). The characteristics of a certain polymer solution are reflected in its phase diagram and the melting curve and crystallization curve. The phase diagram is determined by determination of $T_{liq}$ as a function of polymer concentration. The polymer/solvent combination may further comprise some non-solvent. By adding the non-solvent and by choosing the solvent, the person skilled in the art can tune the phase diagram such that for the choosen combination liquid-liquid phase separation occurs, upon cooling down, at a temperature ($T_{liq}$) that is higher than the crystallization temperature of either the polymer ($T_{c,p}$) or the solvent ($T_{c,s}$). Hence, in an embodiment, the invention is also directed to a method for making a porous scaffold, wherein the solvent of a) further comprises a non-solvent, e.g. wherein the non-solvent comprises a polar non-solvent. For example, this can be a method, wherein the solvent comprises 2-20 wt. % non-solvent, e.g. 2-15 wt %. This amount may depend on the solvent, non-solvent and polymer. In the invention, solvent may also comprise a number of solvents, and non-solvent may also comprise a number of non-solvents. When a solvent/non-solvent mixture is used, $T_{c,s}$ describes the crystallisation temperature of the solvent/non-solvent mixture. When combinations of polymers (polymers) would be used, $T_{c,p}$ describes the crystallisation temperature of the combination of polymers.

When phase diagrams are not known, the method of the invention may also include a determination of one ore more phase diagrams for the polymer/solvent combination (1a) as function of the type of solvent, (1b) as function of the type of solvent combinations and their respective amounts, and where applicable (2a) as function of the type of non-solvent, (2b) as function of the type of non-solvent combinations and their respective amounts. When one uses combinations of polymers, one may also determine phase diagrams (3) as function of the type of polymer combinations and their respective amounts. This can be done with techniques known by the person skilled in the art. Hereby, this person skilled in the art can choose those combinations of polymer/solvent or polymer/solvent/non-solvent that, according to the invention, for the chosen combination liquid-liquid phase separation occurs, upon cooling down, at a temperature ($T_{liq}$) that is higher than the crystallization temperature of either the polymer ($T_{c,p}$) or the solvent ($T_{c,s}$). Here, solvent and non-solvent may also comprise combinations of solvent and non-solvent, respectively. The person skilled in the art can also use both combinations of solvent and non-solvent, and when desired also combinations of polymers (e.g. polymers based on macrodiols with different molecular weights).

The polymer diluent should be cooled to a temperature below $T_{c,p}$. The cooling rate determines the rate at which liquid-liquid phase separation occurs. When liquid-liquid phase separation occurs, polymer poor domains are formed, within the continuous, polymer rich phase. The rate of cooling affects the rate of formation and the size of the polymer poor domains. It has been found that the size and distribution of the polymer poor domains determines the appearance of the micropores in the final porous scaffold. (The micropores also connect the macropores formed where the particulate material used to be.) Thus, by adjusting the cooling rate the size of the polymer poor domains can be influenced. Preferably the cooling rate is chosen in such a way that domains with a diameter over 30 μm are created when the final structure is fixed (for example, when the crystallisation temperature of the polymer has been reached). Porous structures with porosities higher than 60% can be made, and e.g. scaffolds with a porosity of 70 or 80% could be obtained. Cooling to a temperature of about 20 or −18° C. gave good results.

When the domains are not large enough, the cooling rate has to be decreased. The amount of domains can be influenced by increasing the difference between $T_{liq}$ and $T_{c,p}$, for example by adding a non-solvent.

Finally the mixture has to be cooled to below the $T_{cp}$. Crystallisation of the polymer in solution prevents further phase separation and fixates the structure for the final porous scaffold.

After that the solvent or solvent mixture and pore forming material has to be washed out at a temperature below the melting temperature of polymer diluent, $T_m$. A washing agent should be used in which the elastomer does not dissolve (non-solvent). Washing out the solvent and pore forming material can be done in several steps. In the first step the solvent is washed out and thus the washing agent has to be mixable with the solvent mixture. Suitable washing agents for solvents like DMSO, NMP, DMF and dioxane mixed with non-solvent like water, ethanol, or water and ethanol.

When polar non-solvents like diethyl ether, hexane are used, ethanol is a suitable washing agent. Water can still be a good washing agent but needs to be mixed with a certain amount of ethanol to ensure mixing of the non-solvent in the washing agents. When solvents like chloroform are used and for example ethanol, hexane or pentane are used as non-solvent, and a suitable washing agent is ethanol. In the second step the pore forming material is washed out. It is important that the pore forming agent is soluble in the washing agent but that the polymer does not dissolve in the washing agent (non-solvent for polymer). A suitable washing agent for washing out for example saccharose or NaCl, saccharose, or glucose is water. The solvent mixture and the pore forming mixture can also be washed out at once when they are both soluble in the washing agent.

The method for making porous scaffolds provided by the present invention is especially suitable to prepare porous scaffolds of the polyurethanes and polyurethane ureas (made according to the method) of the invention. Suitable solvents for polyurethanes and polyurethane ureas are DMSO, DMF, NMP, cresol, 1,4-dioxane, chloroform. In another embodiment, the invention is directed to a method for making porous scaffolds, wherein the solvent for polyurethanes or polyurethane ureas are selected from the group consisting of DMSO, DMF, NMP, cresol, and chloroform.

It was found that certain combinations of washing agents prevented skin formation and resulted in an open pore structure at the surface, which further improves the porous structure. In this case the skin does not have to be removed before implantation, which improves the method for making a porous scaffold. In a preferred embodiment of the method, washing is performed in successively water/ethanol 80/20, ethanol/water 95/5, and diethyl ether or hexane or pentane. It was found that, for porous scaffolds made on the basis of poly(ε-caprolacton) based polyurethanes, skin formation could be prevented when washing was performed in successively water/ethanol 80/20, ethanol/water 95/5, and diethyl ether or hexane or pentane.

In the invention, the term poly urethane also comprises combinations of poly urethanes, e.g. based on macrodiols having different molecular weights, and poly urethane ureas. Likewise, the terms macrodiols, diols, diamines, diisocyanates may comprise combinations of macrodiols, diols diamines or diisocyanates, respectively. Molecular weights of macrodiols are mean molecular weights. Though a number of embodiments describe elastomers, the invention is not limited to elastomers only.

EXAMPLES

Example 1

Synthesis Polyurethane

All steps were performed under Argon atmosphere. 11.23 g (0.1246 mol) 1,4-butanediol (Aldrich, distilled from 3 Angstrom molsieves) was added to 185.86 g (1.628 mol) ε-caprolactone (Union Carbide, distilled from $CaH_2$ under reduced pressure). This mixture was polymerized to a macrodiol 150° C. for 8 days. 50 ml (0.3229 mol) 1,4-butane diisocyanate (Bayer, distilled under reduced pressure) was added to 56.10 g (0.03546 mol) of the obtained macrodiol. The 1,4-butane diisocyanate and the poly(ε-caprolactone) prepolymer were reacted at 80° C. for 3.5 hours to obtain a macrodiisocyanate. The surplus diisocyanate was distilled off. 60.69 g (0.0326 mol) of the obtained macrodiisocyanate was chain extended with 2.91 g (0.0323 mol) 1,4-butanediol at 80° C. until the intrinsic viscosity was at least 0.8 dl/g.

Example 2

Mechanical Properties

In table 1 tear and tensile strengths of polyurethanes made according to example 1 poly(ε-caprolactone) segments of different length are compared to polyurethanes made according to prior art method where the poly(ε-caprolactone) diol segment was made using 0.08 wt. % stannous octoate as a catalyst (wt catalyst/wt polymer).

Spaans used 0.1 wt. % catalyst for the preparation of the macrodiol, which is equal to 0.08 wt. % catalyst to the polymer for a macrodiol length of 2000 g/mol) (Spaans et. al. Polymer Bulletin, 41, 131-138, 1998, C. J. Spaans, Biomedical Polyurethanes Based On: 1,4-Butanediisocyanate: An Exploratory Study. 2000 PhD Thesis ISBN 90-367-1232-7, chapter 2).

Polymer films were by made according to the procedure described by Spaans (Polymer Bulletin, 4.1., 131-138, 1998) by dissolving the polymer in 1,4-dioxane at 100° C. at a concentration of 6% (w/w). The solvent was removed at 70° C. Last traces of solvent were removed under reduced pressure at 40° C.

The tear strength was determined according a procedure described by De Groot et. al. (Biomaterials, 17: 163-173, 1996) using Instron 4301 tensile tester. Trouser specimens of 3.75 cm long, 1.25 cm wide and with a longitudinal slit of 2.5 cm were used. During testing at room temperature the force was applied normally to the plane, operating a cross-head speed of 250 mm/min.

Tensile testing was performed on rectangular-shaped specimens of about (40×0.75×0.35 mm), cut from films, at room temperature using an Instron tensile (4301) tester at a cross-head speed of 10 mm/min.

TABLE 1

| Polyurethane | Intrinsic viscosity (dl/g) | Tear strength (kJ/m$^2$) | Tensile strength (MPa) |
|---|---|---|---|
| Prior art PU2000[a] | 3.04 | 79 | 23 |
| PU1000[b] | 1.17 | 211 | 38 |
| PU1600[b] | 1.81 | 137 | 44 |
| PU1900[b] | 1.98 | 139 | 55 |
| PU2200[b] | 2.65 | 97 | 38 |

[a]Spaans et. al. Polymer Bulletin, 41, 131–138, 1998; C. J. Spaans, Biomedical Polyurethanes Based On: 1,4-Butane diisocyanate: An Exploratory Study. 2000 PhD Thesis ISBN 90-367-1232-7, chapter 2. Here, polyurethane was made with catalyst. The macrodiisocyanate was chain extended with 1,4-butanediol. Spaans erroneously wrote the tear strength in N/mm. It should have been kJ/m$^2$. Since 1 N/mm = 2 kJ/m$^2$. Hence, the values in N/mm he found, should be divided by a factor 2 (or the N/mm should be changed into kJ/m$^2$.
[b]Polyurethane made according to the invention, made without catalyst. The macrodiisocyanate was chain extended with 1,4-butanediol.

From table 1 it can be concluded that the tear strength of polyurethanes made according to the invention increases with decreasing molecular weight of the poly(ε-caprolactone) segment. A polyurethane made according to the invention, with a molecular weight of the poly(ε-caprolactone) segment of 2000 g/mol will have a tear strength between 97 and 139 kJ/m$^2$, which is higher than the tear strength of the prior art polyurethane, which has a tear strength of 79 kJ/m$^2$. It further appears that polymers according to the invention can have good properties, even with a lower intrinsic viscosity.

A polyurethane made according to then invention, with a molecular weight of the poly(ε-caprolactone) segment of 2000 g/mol will have a tensile strength between 38 and 55 Mpa, which is higher than the tensile strength of the prior art polyurethane, which is 23 Mpa. This is very likely to be comparable to the tensile strength of prior art polyurethane with a longer hard segment.

Example 3

Tear Strength as Function of Intrinsic Viscosity

The tear strength, determined according the procedure described in example 2, of polyurethanes made according to example 1 as a function of intrinsic viscosity was determined. The results are shown in table 2.

TABLE 2

| Polyurethane | Intrinsic viscosity (dl/g) | Tear strength (kJ/m$^2$) |
|---|---|---|
| PU1000$^a$ | 0.39 | 5 |
| PU1000$^a$ | 0.76 | 211 |
| PU1000$^a$ | 0.84 | 213 |
| PU1000$^a$ | 1.18 | 211 |

$^a$polymer made according to the invention. No catalyst was used for the synthesis of the macrodiol. The macrodiisocyanate chain extended with 1,4-butanediol It is shown that the tear strength increases with intrinsic viscosity in the range of 0.39 to 0.76 dl/g. Above 0.76 g/mol, the tear strength is constant.

Example 4

Preperation of Biomedical Porous Materials 19.95 g polymer obtained in example 1 was dissolved in a 33.25 g dimethylsulfoxide (DMSO, Acros, distilled from CaH$_2$)/water mixture at 80° C. under argon. Different water percentages are used. After dissolution, demineralized water was added and subsequently 156.6 g NaCl (Merck, PA), that was sieved over 150 and 355 μm sieves (Wilten, Etten-Leur), was added. The NaCl was preheated at 130° C. to prevent gellation of the polymer solution during mixing. The viscous mass was poured into a mould and cooled down to −18° C. The frozen substance was immersed in a water/ethanol mixture (80/20 vol %) at room temperature for 24 hours, the fluid is refreshed once. Then the substance is immersed in ethanol (96%, Nedalco, Holland) for 1 hour. The porous material was dried in a vacuum stove at 37° C. at 10 mbar for several hours. The total amount of DMSO/water was kept constant but the percentage water was changed in order to change increase $T_{liq}$. From the porous materials Scanning Electron Microscopic photographs (SEM, Jeol 6320 F) were taken.

FIG. 2, 3, 4, show SEM photographs of porous scaffolds with increasing degrees of liquid-liquid phase separation, which was the result of addition of an increasing amount of non-solvent (water). The total polymer concentration was 35 wt. % and was kept constant. The polymer was synthesised from poly(ε-caprolactone) with a molecular weight of 2000 g/dl, 1,4-butane diisocyanate and 1,4-butanediol, made according to example 1. The percentage water in the solvent was 0 wt. % (FIG. 2), 3.8 wt. % (FIG. 3), 6.5 wt. % (FIG. 4) and 7.4 wt.-% (FIG. 5)

The porous scaffold presented in FIG. 2 shows substantially no pores caused by liquid-liquid phase separation. The porous structure is poorly interconnected. The diameter of the interconnections between the larger pores is less than 15 μm. The porous scaffold presented in FIG. 3 shows some pores caused by liquid-liquid phase separation but the pores less than 15 μm are mainly responsible for interconnectivity of the larger pores. The porous scaffold presented in FIG. 4 shows pores caused by liquid-liquid phase separation that have sizes between approximately 50-100 μm. These pores are mainly responsible for the interconnectivity. In this figure, these interconnecting pores are indicated by arrows. The porous scaffold presented in FIG. 5 shows pores caused by liquid-liquid phase separation that have sizes between approximately 50-150 μm. The amount of interconnecting pores is increased compared to the porous scaffold shown in FIG. 4, as well as their size.

Example 5

Preparation of Open-Interconnected Pore Structure at the Surface

A porous scaffold was made according to the procedure described in example 4. In FIG. 6 a SEM micrograph of the surface is shown. At the surface a film is shown which has a very low porosity.

A porous scaffold was made according to the procedure described in example 4 up to the point that the scaffold was washed in ethanol for 1 hour. When the scaffold was then submerged in ether, hexane or pentane, after which is was dried, the surface of the scaffold had an open-interconnect pore structure, which is shown in FIG. 7.

Example 6

Preperation of Scaffold According to Prior Art

A polymer was made according to method of the invention. Subsequently, based on this polymer, polymer scaffolds were made according to the method described in WO9925391. The scaffolds that were obtained had a relatively poorly interconnected pore structure.

Example 7

Formation of Polyurethanes with Different Macrodiols

ε-Caprolactone was purified according procedures described in example 1. 1,4-Butanediol was purified according to the procedure described in example 1. The reaction was performed under nitrogen atmosphere. 2.279 gr 1,4-butanediol (BDO, 25.25 mmol) was reacted with 48.211 gr ε-caprolactone (422.4 mmol) for 7 days at 150° C. The conversion was determined with $^1$H nmr and was 99.5% (Mn=1999 g/mol). L-lactide (Hycail, Nordhorn, The Netherlands) was recrystallized from toluene. 1.202 gr (0.0135 mol) 1,4-Butanediol was reacted with 25.864 gr (0.1794 mol) L-lactide for 7 days at 150° C. The convension was determined with $^1$H nmr and was 98.5%. Trimethylene carbonate (Boehringer, Ingelheim, Germany) was recrystallized from o-xylene. 27.64 gr TMC (0.2708 mol) and 1.735 gr BDO (0.01925 mol) was reacted for 5 days. According to 1H nmr, the conversion was 99.5%. Ring opening polymerization can thus be performed without the use of a catalyst.

The macrodiols were endcapped with 1,4-butanediisocyanate according to the procedure described in example 1. Chain extension of the macrodiisocyanates with 1,4-butanediol was performed according to the procedure described in example 1, until the intrinsic viscosity of the polymer was at least 0.8 g/dl.

Example 8

Synthesis Polyurethanes with Different Amount of Catalyst

Polycaprolactone prepolymers (2000) were made with different amounts of the catalyst stannous octoate (Sn(Oct)$_2$).

The percentage $Sn^{2+}$ was determined by titration and was 20-24 wt.-%. For this experiment a dilution series of stannous octoate in ϵ-caprolactone in volumetric glassware was made. For the stock I solution, 0.00534 g of stannous octoate was diluted in 10 ml ϵ-caprolactone resulting in a 0.000534 g/ml solution. One ml of this solution was diluted with 9 ml of ϵ-caprolactone resulting in a 0.0000534 g/ml stock II solution. (2.8 ml of this solution will give 0.00015 g of stannous octoate). A typical example of a prepolymerization. The prepolymer was synthesized with 2.8 ml of the stock II solution and ~26 ml ϵ-caprolactone (total: 29.937 g (0.2623 mole) and 1.415 g (0.0157 mole) of the initiator 1,4-butanediol. The reaction-mixture was stirred for one hour at 155° C. and the reaction was continued in an oven for 7 days at 155° C. This results in a prepolymer with a mean molecular weight of 1997 g/mole with 0.00048 wt % stannous octoate. Polycaprolacton with respectively 0, 0.00001, 0.0001, 0.0005 and 0.1 wt.-% was made.

The prepoplymers were then endcapped with BDI according to the procedure described in example 1. Typical amounts of the endcapping procedure are: 27.026 g (0.01353 mole) prepolymer is stirred for 3.5 hours at 80° C. with 25.237 gram BDI (0.1801 mole). This is a 13.3 fold excess. The unreacted BDI is distilled of at 0.01 mbar, 75° C. for 19 hours. The stoichiometric amount of reacted BDI can be calculated and any extra reacted BDI is determined by weighing. In this case, the expected amount of reacted BDI is 3.792 g (13.53 mmole×2×140.142 (molweight BDI)). The weighed amount is 3.921 g; an excess of 0.129 g (3.4% of 3.792 g).

In FIG. 8, the extra amount of BDI that could not be removed, is presented as function of the stannous octoate concentration. At low concentrations (0 and 0.0001 wt.-%) the additional amount BDI that could not be distilled of was 0.5±1% (average of 4). With increasing catalyst concentration this amount increases to 8.7±wt.-% at 0.1 wt.-% stannous octoate. An increase in $Sn(Oct)_2$ concentration causes an increase in side reactions.

The isocyanate endcapped prepolymers were then chain extended with BDO according to the procedure (described in example 1). Typical amounts of a chain extension procedure are: 25,397 gr (0.01115 mol) endcapped PCL (molwt. PCL1996 g/mol, molwt endcapped PCL 2277, 0.0005 wt.-% $Sn(Oct)_2$) and 1,023 gr (0.01135 mol) BDO. The polymers made with no $Sn(Oct)_2$ and a $Sn(Oct)_2$ concentration of 0.0001 wt.-% in the prepolymer were soluble. Polymers made with a $Sn(Oct)_2$ concentration of 0.0005 wt.-% and 0.1 wt.-% in the prepolymers were not soluble as is indicated in FIG. 8.

Example 9

Synthesis Polyurethanes with Different End-Cap Temperatures

Polycaprolactone (1600) prepolymers were was made according to the procedure described in example 1. Prepolymers were encapped during 3.5 hours at different temperatures respectively 80° C., 85° C., 90° C. and 100° C. and 120° C. According to the procedure described in example 1, the prepolymers were encapped with BDI and the excess BDI was removed. The amount of additional unremovable BDI was determined according to example 8. In FIG. 9 the amount of additional unremovable BDI as a function of encap temperature is shown. The number of additional unremovable BDI cause by side reactions increases with increasing endcap temperature. The endcapped prepolymers were then chain extent with BDO according to the procedure in example 1. The polymers of which the prepolymers were endcapped at 80° C. and 85° C. were soluble. The polymers of which the prepolymers were endcapped at 90° C. and 100° C. and 120° C. were less or not soluble.

Typical amounts of the endcap procedure at 100° C.: 13.745 g (8.587 mmole) of PCL 1600.7 g/mol is stirred for 3.5 hours at 100° C. with 15.327 g (0.1094 mole) BDI. This is a 12.7 fold excess. The unreacted BDI is distilled of at 0.01 mbar, 75° C. for 19 hours. The stoichiometric amount of reacted BDI can be calculated and any extra reacted BDI is determined by weighing. In this case the expected amount of reacted BDI is 2.407 g (8.587 mmole×2×140.142 (M BDI)). The weighed amount is 2.460 g; an excess of 53 mg (2.2% of 2.407 g).

Example 10

Polymerization (Chain Extention) at Different Temperatures

Polycaprolactone (1600+2000) prepolymers were made and endcapped according to the procedure described in example 1. The endcapped prepolymers were then chain-extended with BDO according to the procedure in example 1 at 6 different temperatures and times: 80° C., 16 h.; 100° C., 16 h.; 110° C., 14 h.; 130° C., 8 h.; 150° C. 4.5 h. and 180° C., 3 h. Polymers made at a temperature of 130° C. or lower were soluble. When the chain extention step was performed at 150° C. or 180° C., a less or non soluble polymer was obtained caused by side reactions occuring at these temperatures.

Example 11

Synthesis Polyurethanes in Solution

Polycaprolactone (2000) prepolymers were made and endcapped according to the procedure described in example 1. The endcapped prepolymers were then dissolved in dimethyl sulfoxide (50 wt %) and then chain extended with BDO at a temperature of 100° C. for 24 hours. The reaction mixture was then diluted with dimethyl sulfoxide to a 5% solution. After precipitation in water and rinsing with alcohol, the polymer was dried at 40° C. under reduced pressure. This resulted in polyurethanes with an intrinsic viscosity of 1.0 dl/g. Typical amounts of the polyurethane synthesis in solution are as follows: 17.509 g (0.007665 mol) of endcapped PCL (2004 g/mol; 2284.3 g/mol endcapped), 19.3 g of dimethylsulfoxide and 0.701 g (0.07778 mol) of 1,4-butanediol.

Example 12

Synthesis Polyurethanes in Solution According to Prior Art (Polymer Bulletin 41, 131-138, 1998)

A Polycaprolactone prepolymer with a $Sn(Oct)_2$ concentration of 0.1 wt.-% was made according to the procedure described in example 8. According to FIG. 8, the percentage of extra BDI that had reacted during the endcap procedure was 8.7 percent. Chain extention with BDO was performed in DMSO at a concentration of 25 wt.-% at 80° C. When the reaction mixture became viscous, more solvent was added to keep the system homogeneously. The mixture was stirred for an additional 10 hours and subsequently diluted to 1-2 wt.-% solution. The polymer was precipitated in water and dried to constant mass at 40° C. under reduced pressure.

In contrast to bulk polymerization, in solution no crosslinking took place with a stannousoctoate concentration of 0.1 wt.-%. However, as could be concluded from example 8, this catalyst concentration gives rise to side reactions, which results in poorer mechanical properties as is indicated in example 2.

Example 13

Melting Temperatures and Melting Enthalpies of Polyurethanes According to the Invention Compared to Prior Art Polyurethanes In table 3 the urethane hard segment melting temperatures and melting enthalpies of respectively the polyurethanes made according to the invention and described in example 2 (table 1), and prior art (Pol. Bul. 41, 131-138, 1998). Polymer films were made according to Spaans et. al. (Pol. Bul. 41, 131-138, 1998) as described in example 2. It can be concluded that polyurethanes made according to the invention have higher melting temperatures of the urethane hard segments for comparable soft segment content (Tm between 79.5 and 87.4° C.) compared to the prior art polyurethane (Tm=68.5). The melting enthalpy of the polyurethanes according to the invention is also higher (between 15.0 and 15.4 J/g) compared to prior art polyurethanes (11.2 J/g). This is due to the fact that polyurethane according to the invention show less side reaction in the synthesis due to the absence of a catalyst, which results in more linear polymers, and results in better packing of the urethane hard segments. The higher melting temperature and melting enthalpies are responsible for the better mechanical properties of the polyurethanes made according to the invention, see also table 3.

TABLE 3

| Polyurethane | Melting temperature urethane hard segment (° C.) | Melting enthalpy urethane hard segment (J/g) |
| --- | --- | --- |
| Prior art PU2000[a] | 68.5 | 11.2 |
| PU1000[b] | 109.9 | 38.4 |
| PU1600[b] | 94.0 | 22.3 |
| PU1900[b] | 87.4 | 15.4 |
| PU2200[b] | 79.5 | 15.0 |

[a]prior art polyurethane, table 1
[b]polyurethanes made according to the invention, table 1

Example 14

Polymerization by Reaction of Macrodiol and Reaction Product of Diisocyanate and Chain Extender According to Prior Art (Pol. Bul. 41, 131-138, 1998)

Poly(ε-caprolactone) prepolymer (1500) was made with stannous octoate (0.1 wt.-%) according to example 8. An isocyanate terminated urethane block (BDI-BDO-BDI) was made by mixing 1,4-butanediisocyanate with 1,4-butanediol in a mol ratio of 12:1, without the use of a catalyst. The mixture was reacted for 5 hours at 80° C. The excess BDI was removed by washing with dry hexane.

The prepolymer and isocyanate block were separately dissolved in DMSO. The block solution was slowly added to the prepolymer solution at 80° C. After adding the polymer solution was 30%. After addition, the components were reacted at 80° C. for another 5 hour. The polymer solution became opaque and only a slight increase in viscosity was observed. After reaction the polymer solution was diluted to ~5 wt.-% and the polymer solution was precipitated in water, rinsed with ewthanol and dried in a vacuum stove at 40° C. The intrinsic viscosity of the polymer was 0.4 dl/g. Increasing the polymerization temperature to 100° C. also resulted in a opaque polymer solution with slightly increased viscosity.

Example 15

Polymerization by Reaction of Macrodiol and Reaction Product of Diisocyanate and Chain Extender According to the Invention Poly(ε-caprolactone) prepolymer (1500) was made without the use of a catalyst according to example 1 and 7. The isocyanate block (BDI-BDO-BDI) was made according to example 14. The prepolymer and isocyanate block were dissolved in DMSO to a concentration of 75 wt.-% at 120° C. for 24 hours. The polymer solution was then diluted and precipitated according to example 14. The intrinsic viscosity of the polymer was 0.9 dl/g. Polymerization was also performed at 100° C. in the bulk (without solvent) for 24 hours. The intrinsic viscosity of the polymer was 0.8 dl/g.

Example 16

Preparation Porous Materials According to Prior Art

FIG. 2 shows a similar SEM photograph of a porous material when made according to prior art ((WO99/25391). The preparation procedure is described in example 4 WO99/25391. The pores are not highly interconnected. The viscous mixture (polymer/solvent/NaCl) was frozen at −18° C. and the frozen substance was washed at room temperature. Even when the solvent mixture was not frozen and the viscous mixture (polymer/solvent/NaCl) was cooled to room temperature and left at room temperature for 1 hour, after which the substance was washed at room temperature, the porous structure was comparable to that presented in FIG. 2. The pores were not well interconnected. This may be due to the fact that in this example according to example 4 of WO99/25391, phase inversion takes place when the (frozen) substance is washed, whereas in the invention, phase inversion takes place earlier during cooling down homogeneous solution of the elastomer in a solvent according to the invention at a rate that allows liquid-liquid phase separation (step c), and not later during the washing step (d). In FIG. 10 a, the crystallization temperature was found to be below room temperature and open-pore structure could have been expected but it appeared that during the 0.5 hour at room temperature crystallization of the polymer took place and the structure was fixed.

Example 17

Determination Phase Diagram Polyurethane in Relation to Porous Structure Described in Example 4

Phase diagrams were determined for polymer solutions containing 0%, 3.8% and 7.4% water in DSMO. First porous materials were made according to the procedure described in example 4. The polymer of the porous materials was then used to determine the phase diagrams. The molecular weight of the polymer, with which the porous materials were made is thus the same as for the polymer with which the phase diagram is determined. Melting temperatures of the polymer solutions were determined by DSC (TA-instrument 2920 modulated DSC) The samples were homogenized at 80° C. for 45 minutes. Prior to cooling, the sample was heated to 95° C., then cooled to temperature and then heated. Heating and cooling rates were 1° C./min. Cloud points, as an indication of liquid-liquid phase separation, were determined by dissolving the polymer in water/DMSO at 80° C. The air bubbles were removed by applying vacuum with a syringe. The polymer solutions were then cooled at a rate of 0.5° C./min until the cloud point was reached.

In FIG. 10 the phase diagrams of polymer solution with no water (a), 3.8% water (b) and 7.4% water (c) are shown. When no water is added, no liquid-liquid phase separation takes place before the polymer solution crystallizes. The corresponding porous structure is presented in FIG. 2 (see example 4). When 3.8% water is added, liquid-liquid phase separation takes place before crystallization of the polymer. Point B as indicated in FIG. 1 is positioned at concentration of 42% (in FIG. 10b). The porous material is made at a polymer concentration of 35/42 B (0.83 B). The corresponding porous structure is presented in FIG. 4 (see example 4). When the percentage of water is increased to 7.4%, the liquid-liquid phase diagram has moved to higher temperatures. Point B as indicated in FIG. 1 is now positioned at concentration of 70%. The porous material is made at a concentration of 35/70 B (0.5 B). The corresponding porous material is presented in FIG. 5.

The invention claimed is:

1. A method for making a porous scaffold from a polymer, the polymer comprising a polyurethane obtained by a process comprising:
    1a) reacting either a macrodiol or a chain extender with an excess of diisocyanate, resulting in a macrodiisocyanate or a reaction product of the diisocyanate and the chain extender,
    1b) removing the remaining unreacted diisocyanate, and
    1c) reacting, the macrodiisocyanate with the chain extender or the macrodiol with the reaction product,
wherein a) and c) are carried out in the substantial absence of a catalyst: the method for making a porous scaffold comprising:
    2a) providing a homogeneous solution of the polymer in a solvent wherein the polymer-solvent combination is chosen in such a way that for the chosen combination liquid-liquid phase separation occurs, upon cooling down, at a temperature ($T_{liq}$) that is higher than the crystallization temperature of either the polymer ($T_{c,p}$) or the solvent ($T_{c,s}$),
    2b) adding a particulate material that is insoluble in the solvent,
    2c) cooling down the mixture obtained in b) at a rate that allows liquid-liquid phase separation to result in the desired micropore morphology for the porous scaffold, to a temperature below the crystallization temperature of either the polymer ($T_{c,p}$) or the solvent ($T_{c,s}$), and
    2d) washing the mixture obtained in c) with a non-solvent, wherein the polymer is insoluble, but wherein the particulate material can be dissolved, at a temperature below the melting temperature of the polymer in solution ($T_{m,p}$), or at a temperature below the melting temperature of the solvent ($T_{m,s}$), for a time sufficient to allow dissolution of the particles of the particulate material.

2. Method according to claim 1, wherein a solution is used with a polymer concentration between $0.4 C_B$ and $0.9 C_B$, $C_B$ being the concentration of a particular polymer in solution, for which the temperature at which liquid-liquid phase separation occurs ($T_{liq}$) is equal to the crystallization temperature of the polymer in solution($T_{c,p}$).

3. Method according to claim 2, wherein a solution is used with a polymer concentration between $0.4 C_B$ and $0.8 C_B$.

4. Method according to claim 1, wherein washing is successively performed with water/ethanol 80/20, ethanol/water 95/5, and then with either diethyl ether or hexane or pentane.

5. Method according to claim 1, wherein the solvent of 2a) further comprises a non-solvent.

6. Method according to claim 5, wherein the solvent comprises non-solvent in an amount of 2-20% by weight of the amount of solvent.

7. Method according to claim 1, wherein the polymer is an elastomer.

8. Method according to claim 1, wherein the macrodiol is reacted with an excess of a diisocyanate to obtain a macrodiisocyanate.

9. Method according to claim 1, wherein the macrodiol is synthesised in a catalyst-free method.

10. Method according to claim 1, wherein the macrodiol has a molecular weight between 1000 and 3000 g/mol.

11. Method according to claim 1, wherein the macrodiol is the product of a ring-opening polymerization.

12. Method according to claim 11, wherein the macrodiol is a polytetramethylene carbonate.

13. Method according to claim 11, wherein the macrodiol is a polylactide.

14. Method according to claim 11, wherein the macrodiol is a poly($\epsilon$-caprolactone)diol.

15. Method according to claim 14, wherein the poly($\epsilon$-caprolactone)diol has a molecular weight of 1000-2200g/mol.

16. Method according to claim 1, wherein the chain extender is 1,4-butanediol.

17. Method according to claim 1, wherein the chain extender is a reaction product of two diol molecules and one diisocyanate molecule.

18. Method according to claim 1, wherein the diisocyanate is a(cyclo)aliphatic diisocyanate.

19. Method according to claim 18, wherein the diisocyanate is 1,4-butane diisocyanate.

20. Method according to claim 1, wherein the catalyst concentration is below 0.001 wt.-% (wt. catalyst/wt. polyurethane).

21. Method according to claim 1, wherein 1a) is carried out at a temperature below 120° C.

22. Method according to claim 1, wherein 1c) is carried out at a temperature below 180° C.

23. Method for making a porous scaffold comprising:
    a) providing a homogeneous solution of a polyurethane in a solvent wherein the polyurethane-solvent combination is chosen in such a way that for the chosen combination liquid-liquid phase separation occurs, upon cooling down, at a temperature ($T_{liq}$) that is higher than the crystallization temperature of either the polyurethane ($T_{c,p}$) or the solvent ($T_{c,s}$),
    b) adding a particulate material that is insoluble in the solvent,
    c) cooling down the mixture obtained in b) at a rate that allows liquid-liquid phase separation to result in the desired micropore morphology for the porous scaffold, to a temperature below the crystallization temperature of either the polyurethane ($T_{c,p}$) or the solvent ($T_{c,s}$), and
    d) washing the mixture obtained in c) with a non-solvent, wherein the polyurethane is insoluble, but wherein the particulate material can be dissolved, at a temperature below the melting temperature of the polyurethane in solution ($T_{m,p}$), or at a temperature below the melting temperature of the solvent ($T_{m,s}$), for a time sufficient to allow dissolution of the particles of the particulate material.

24. A porous scaffold prepared by a process comprising:
a) providing a homogeneous solution of a polyurethane in a solvent wherein the polyurethane-solvent combination is chosen in such a way that for the chosen combination liquid-liquid phase separation occurs, upon cooling down, at a temperature ($T_{liq}$) that is higher than the crystallization temperature of either the polyurethane ($T_{c,p}$) or the solvent ($T_{c,s}$),
b) adding a particulate material that is insoluble in the solvent,
c) cooling down the mixture obtained in b) at a rate that allows liquid-liquid phase separation to result in the desired micropore morphology for the porous scaffold, to a temperature below the crystallization temperature of either the polyurethane ($T_{c,p}$) or the solvent ($T_{c,s}$), and
d) washing the mixture obtained in c) with a non-solvent, wherein the polyurethane is insoluble, but wherein the particulate material can be dissolved, at a temperature below the melting temperature of the polyurethane in solution ($T_{m,p}$), or at a temperature below the melting temperature of the solvent ($T_{m,s}$), for a time sufficient to allow dissolution of the particles of the particulate material.

25. The porous scaffold according to claim 24, wherein the polyurethane is prepared by a process comprising:
a) reacting either a macrodiol or a chain extender with an excess of diisocyanate, resulting in a macrodiisocyanate or a reaction product of the diisocyanate and the chain extender,
b) removing the remaining unreacted diisocyanate, and
c) reacting, the macrodiisocyanate with the chain extender or the macrodiol with the reaction product,
wherein a) and c) are carried out in the substantial absence of a catalyst.

* * * * *